United States Patent
Pericas-Brondo et al.

(10) Patent No.: US 8,299,113 B2
(45) Date of Patent: Oct. 30, 2012

(54) BICYCLIC TETRAHYDROPYRROLE COMPOUNDS

(75) Inventors: Miguel Angel Pericas-Brondo, Esplugues de l.lobregat (ES); Antonio Torrens-Jover, Terrassa (ES); Susana Yenes-Minguez, Molins de Rei (ES); Félix Cuevas Cordobes, Madrid (ES); Carmen Garcia Granda, Madrid (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 795 days.

(21) Appl. No.: 12/226,626

(22) PCT Filed: Apr. 30, 2007

(86) PCT No.: PCT/EP2007/003826
§ 371 (c)(1), (2), (4) Date: Mar. 18, 2009

(87) PCT Pub. No.: WO2007/128458
PCT Pub. Date: Nov. 15, 2007

(65) Prior Publication Data
US 2010/0029738 A1 Feb. 4, 2010

(30) Foreign Application Priority Data
Apr. 28, 2006 (EP) .................... 06384008
Dec. 7, 2006 (EP) .................... 06025366

(51) Int. Cl.
*A01N 43/38* (2006.01)
*A61K 31/40* (2006.01)
*C07D 209/00* (2006.01)

(52) U.S. Cl. ............................. 514/412; 548/452
(58) Field of Classification Search .................. 514/412; 548/452
See application file for complete search history.

(56) References Cited

U.S. PATENT DOCUMENTS
5,359,087 A 10/1994 Johnson et al.

FOREIGN PATENT DOCUMENTS
EP 0648762 A2 4/1995

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Matsuno et al. "SA4503, a novel cognitive enhancer, with alpha 1 receptor agonistic properties" Behavioural Brain Research, 1997, vol. 83, pp. 221-224.*
Morissette et al. "High-throughput crystallization: polymorphs, sals, co-crysals and solvates of pharmaceutical solids" Advanced Drug Delivery Reviews, 2004, vol. 56, pp. 275-300.*
Yang Q., et al. "Lewis Acid Assisted Ring-Closing Metathesis of Chiral Diallylamines: An Efficient Approach to Enantiopure Pyrrolidine Derivatives" Organic Letters, 2005, vol. 7, No. 5, pp. 871-874.
Dieltiens N., et al. "Pyrrole synthesis using a tandem Grubbs' carbene-$RuCl_3$ catalytic system" Tetrahedron Letters, 2004, 45:8995-8998.
International Search Report issued by the International Searching Authority (ISA/EP) on Sep. 12, 2007 in connection with International Application No. PCT/EP2007/003826.
Written Opinion of the International Searching Authority issued by the International Searching Authority (ISA/EP) on Sep. 12, 2007 in connection with International Application No. PCT/EP2007/003826.
WO 2005/005417 A1 (Astrazeneca AB et al) Jan. 20, 2005.
WO 2004/013117 A1 (Charterhouse Therapeutics Ltd. et al.) Feb. 12, 2004.
Monnet et al., "The $Sigma_1$ Protein as a Target for the Non-genomic Effects of Neuro (active) steroids: Molecular, Physiological, and Behavioral Aspects" J. Pharmacol Sci 100:93-118 (2006).
Cendan et al., "Formalin-Induced Pain is Reduced in $\sigma_1$ Receptor Knockout Mice" European Journal of Pharmacology 511:73-74 (2005).
Alonso et al., "Immunocytochemical Localization of the $Sigma_1$ Receptor in Adult Rat Central Nervous System" Neuroscience vol. 97, No. 1:155-170 (2000).
Ovalle et al., "Fibroblast Growth Factor-2 is Selectively Modulated in the Rat Brain by E-5842, A Preferential Sigma-1 Receptor Ligand and Putative Atypical Antipychotic" European Journal of Neuroscience 13:909-915 (2001).
Cendan et al., "Antinociceptive Effects of Haloperidol and its Metabolites in the Formalin Test in Mice" Psychopharmacology 182:485-493 (2005).
Monnet, "Sigma-1 Receptor as Regulator of Neuronal Intracellular $Ca^{2+}$ : Clinical and Therapeutic Relevance" Biol. Cell 97:873-883 (2005).
Mei et al., "$\sigma_1$ Receptor Modulation of Opioid Analgesia In The Mouse" The Journal of Pharmacology and Experimental Therapeutics vol. 300, No. 4:1070-1074 (2002).

* cited by examiner

*Primary Examiner* — Sreeni Padmanabhan
*Assistant Examiner* — Kendra D Carter
(74) *Attorney, Agent, or Firm* — John P. White; Cooper & Dunham LLP

(57) ABSTRACT

The present invention relates to substituted bicyclic tetrahydropyrrole compounds of general formula (I), methods for their preparation, medicaments comprising these compounds as well their use in the manufacture of a medicament for the treatment of humans and animals.

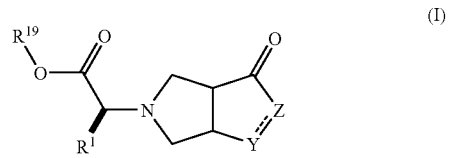

(I)

36 Claims, No Drawings

BICYCLIC TETRAHYDROPYRROLE COMPOUNDS

This application is a §371 national stage of PCT International Application No. PCT/EP2007/003826, filed Apr. 30, 2007, and claims priority of European Patent Applications Nos. 06025366.3, filed Dec. 7, 2006 and 06384008.6, filed Apr. 28, 2006, the contents of all of which are hereby incorporated by reference into this application.

FIELD OF THE INVENTION

The present invention relates to compounds having pharmacological activity towards the sigma (σ) receptor, and more particularly to some bicyclic tetrahydropyrrole derivatives, to processes of preparation of such compounds, to medicaments comprising them, and to their use in therapy and prophylaxis, in particular for the treatment of Alzheimer's disease.

BACKGROUND OF THE INVENTION

Alzheimer's disease (AD) is a progressive, irreversible brain disorder with no known cause or cure. Symptoms of the disease include memory loss, confusion, impaired judgment, personality changes, disorientation, and loss of language skills. Always fatal, Alzheimer's disease is the most common form of irreversible dementia.

According to the American Health Assistance Foundation (AHAF), more than 4.5 million Americans are believed to have Alzheimer's disease and by 2050, the number could increase to 13.2 million. In every nation where life expectancy has increased, so has the incidence of Alzheimer's disease. Alzheimer's disease is becoming tragically common. It is estimated that there are currently 18 million people worldwide with Alzheimer's disease. This figure is projected to nearly double by 2025 to 34 million people.

Considering the fact that there is at present no effective treatment for this fatal disease, it is an imperative to find new solutions to treat AD.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

Therefore, compounds binding to the sigma receptor and which are suitable for modulating these receptors are useful in the prevention and/or the treatment of diseases associated with the sigma receptor.

Recently it has been found that the sigma-1 receptor may be involved in the pathologenesis of Alzheimer's disease (Uchida et al., Am J Geriatr Psychiatry 2005; 13:1062-1066).

Thus, it was an objective of the present invention to provide new compounds for the use as active ingredients in medicaments. In particular, these active ingredients should be suitable to modulate the sigma receptor, more particularly the sigma-1 receptor.

Said objective was achieved by providing substituted bicyclic tetrahydropyrrolidine compounds of general formula (I) given below, their stereoisomers, corresponding salts and corresponding solvates thereof.

Thus, one of the aspect of the present invention relates to substituted bicyclic tetrahydropyrrolidine compounds of general formula (I)

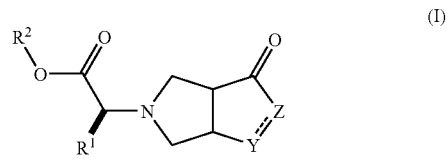

wherein
  $R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group;
  wherein the bond between Y and Z may be unsaturated (Y═Z) or saturated (Y—Z);
  in case of Y and Z being (Y═Z), Y represents CH and Z represents C—$R^6$; C—CHR$^7$R$^{7a}$; a C—(C═O)—$R^8$ group; a C—CH$_2$(SO$_2$)—$R^9$ group; a C—CH$_2$(SO$_2$)—NR$^{10}$R$^{10a}$ group; or a C—(C═O)—NR$^{10}$R$^{10a}$ group;
  in case of Y and Z being (Y—Z), Y represents CH$_2$; C—R$^{11}$R$^{12}$; a CH—(C═O)—R$^{16}$ group; a CH—(SO$_2$)—R$^{17}$ group; CH—(SO$_2$)—NR$^{18}$R$^{18a}$ group; or a CH—(C═O)—NR$^{18}$R$^{18a}$ group and Z represents CH—R$^6$; CH—CHR$^7$R$^{7a}$; a CH—(C═O)—R$^8$ group; a CH—CH$_2$(SO$_2$)—R$^9$ group; a CH—CH$_2$(SO$_2$)—NR$^{10}$R$^{10a}$ group; or a CH—(C═O)—NR$^{10}$R$^{10a}$ group;
  $R^2$, $R^3$, $R^4$, and $R^6$ represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^5$, $R^{5a}$, identical or different, represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^7$, $R^{7a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^8$, $R^9$, $R^{13}$, $R^{14}$, $R^{15}$, $R^{16}$ and $R^{17}$ represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{10}$, $R^{10a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{11}$ and $R^{12}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; a —(SO$_2$)—R$^{13}$-group; or a $R^{14}R^{15}$-group;

$R^{18}$ and $R^{18a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{19}$ represent a hydrogen atom; a linear or branched, saturated or unsaturated, optionally at least mono-substituted aliphatic group; an unbranched or branched, saturated or unsaturated, optionally at least monosubstituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred aspect of the invention the following proviso applies:
if $R^{19}$ is methyl,
and Y and Z are (Y═Z)
and Y represent CH,
Z may not represent a CH group.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$ or $^{14}C$-enriched carbon or $^{15}N$-enriched nitrogen are within the scope of this invention.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radioactive ligands being replaced, and can also be used for modeling physiological actions related to sigma receptors.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids and in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

In general the term "unbranched", especially as used in connection with "aliphatic radical" and "alkyl radical" is to be understood as also meaning and being equivalent to "linear" meaning a not branched chain of C-atoms.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprises saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

"Optionally at least one heteroatom as ring member" is defined as having no heteroatom as ring member, one heteroatom as ring member or more than one heteroatom as ring member.

"Optionally at least mono-substituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

"Optionally mono- or polysubstituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

"Optionally substituted" is defined as no hydrogen radical in the mentioned radical being substituted by another radical, e.g. Cl, F, etc., or one hydrogen radical in the mentioned radical being substituted by another radical, e.g. Cl, F, etc. or more than one hydrogen radical in the mentioned radical being substituted by another radical, e.g. Cl, F, etc. (polysubstituted).

Cyclyl groups/radicals, as defined in the present invention, comprise any saturated, unsaturated or aromatic carbocyclic ring systems which contain optionally at least one heteroatom as ring member and which are optionally at least monosubstituted. Cyclyl groups preferably comprise aryl, heteroaryl, cycloalkyl, heterocyclyl and/or spiro ring systems.

Heterocyclyl groups/radicals, as defined in the present invention, comprise any saturated, unsaturated or aromatic carbocyclic ring systems which are optionally at least monosubstituted and which contain at least one heteroatom as ring member. Preferred heteroatoms for these heterocyclyl groups are N, S or O.

Aliphatic radicals/groups, as referred to in the present invention, are optionally mono- or polysubstituted and may be branched or unbranched, saturated or unsaturated. Unsaturated aliphatic groups, as defined in the present invention, include alkenyl and alkinyl radicals. Saturated aliphatic groups, as defined in the present invention, include alkyl radicals Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-4}$ alkyl group, a linear or branched $C_{1-4}$ alkoxy group, F, Cl, I, Br, $CF_3$, $CH_2F$, $CHF_2$, CN, OH, SH, $NH_2$, oxo, (C=O)R', SR', SOR', $SO_2$R', NHR', NR'R" whereby R' and optionally R" for each substituent independently represents a linear or branched $C_{1-6}$alkyl group.

Alkyl radicals, as referred to in the present invention, are saturated aliphatic radicals. They may be linear or branched and are optionally substituted.

In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—; $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—; $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

Cycloalkyl radicals, as referred to in the present invention, are understood as meaning saturated and unsaturated (but not aromatic), cyclic hydrocarbons, which can optionally be unsubstituted, mono- or polysubstituted. In these radicals, for example $C_{3-4}$-cycloalkyl represents $C_3$- or $C_4$-cycloalkyl, $C_{3-5}$-cycloalkyl represents $C_3$-, $C_4$- or $C_5$-cycloalkyl, etc. With respect to cycloalkyl, the term also includes saturated cycloalkyls in which optionally at least one carbon atom may be replaced by a heteroatom, preferably S, N, P or O. However, mono- or polyunsaturated, preferably monounsaturated, cycloalkyls without a heteroatom in the ring also in particular fall under the term cycloalkyl as long as the cycloalkyl is not an aromatic system. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-8}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl.

Examples for cycloalkyl radicals preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, pyrroline, pyrrolidine, pyrrolidineone, pyrazoline, pyrazolinone, oxopyrazolinone, aziridine, acetidine, tetrahydropyrrole, oxirane, oxetane, dioxetane, tetrahydrofurane, dioxane, dioxolane, oxathiolane, oxazolidine, thiirane, thietane, thiolane, thiane, thiazolidine, piperidine, piperazine or morpholine.

Cycloalkyl radicals, as defined in the present invention, are optionally mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2$R', NHR', NR'R" whereby R' and optionally R" for each substituent independently represents a linear or branched $C_{1-6}$-alkyl group.

An aryl radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-4}$ alkyl group, a linear or branched $C_{1-6}$ alkoxy group, an optionally at least mono-substituted phenyl group, F, Cl, I, Br, $CF_3$, $CH_2F$, $CHF_2$, CN, OH, SH, $NH_2$, oxo, (C=O)R', SR', SOR', $SO_2$R', N(C=O)—OR', NHR', NR'R" whereby R' and optionally R" for each substituent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

An alkyl-aryl radical, as defined in the present invention, comprises a linear or branched, optionally at least monosubstituted alkyl chain which is bonded to an aryl group, as defined above. A preferred alkyl-aryl radical is a benzyl group, wherein the alkyl chain is optionally branched or substituted. Preferred substituents for alkyl-aryl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

A heteroaryl radical is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2$R', NHR', NR'R" whereby R' and optionally R" for each substitutent independently represents a linear or branched $C_{1-6}$-alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidazole, carbazole and quinazoline.

An alkyl-heteroaryl (or alkyl-heterocyclyl) radical, as defined in the present invention, comprises a linear or branched, optionally at least mono-substituted alkyl chain which is bonded to an heteroaryl (heterocyclyl) group, as defined above.

With respect to compounds of general formula (I) of the present invention, Y and Z may form an unsaturated (Y=Z) or a saturated (Y—Z) bond which is illustrated below.

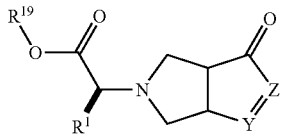
(Y=Z)

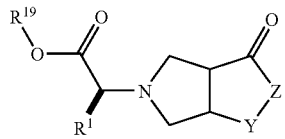
(Y-Z)

A preferred embodiment of the present invention are compounds of general formula (Ia)

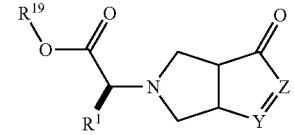
(Ia)

in which
Y represents CH and Z represents C—$R^6$; C—$CHR^7R^{7a}$; a C—(C=O)—$R^8$ group; a C—$CH_2(SO_2)$—$R^9$ group; a C—$CH_2(SO_2)$—$NR^{10}R^{10a}$ group; or a C—(C=O)—$NR^{10}R^{10a}$ group;
and
$R^1$, $R^6$, $R^7$, $R^{7a}$, $R^8$, $R^9$, $R^{10}$, $R^{10a}$ and $R^{19}$ are defined as above.

Another preferred embodiment of the present invention are compounds of general formula (Ib),

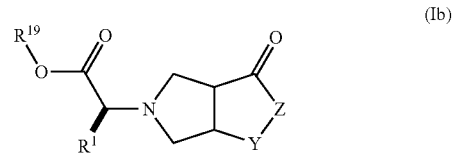
(Ib)

in which
Y represents $CH_2$; C—$R^{11}R^{12}$; a CH—(C=O)—$R^{16}$ group; a CH—$(SO_2)$—$R^{17}$ group; CH—$(SO_2)$—$NR^{18}R^{18a}$ group; or a CH—(C=O)—$NR^{18}R^{18a}$ group
and Z represents CH—$R^6$; CH—$CHR^7R^{7a}$; a CH—(C=O)—$R^8$ group; a CH—$CH_2(SO_2)$—$R^9$ group; a CH—$CH_2(SO_2)$—$NR^{10}R^{10a}$ group; or a CH—(C=O)—$NR^{10}R^{10a}$ group;
and
$R^1$, $R^6$, $R^7$, $R^{7a}$, $R^8$, $R^9$, $R^{10}$, $R^{10a}$, $R^{11}$, $R^{12}$, $R^{16}$, $R^{17}$, $R^{18}$, $R^{18a}$ and $R^{19}$, are defined as above.

A preferred embodiment of the present invention are compounds of general formula (Ia), wherein
Z represents C—$R^6$, thus leading to the compounds being of a structure according to general formula (Iaa)

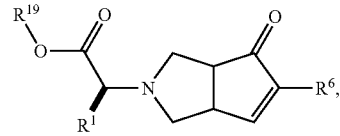
(Iaa)

with $R^1$, $R^6$ and $R^{19}$ being defined as above.

Another preferred embodiment of the present invention are compounds of general formula (I), (Ia), (Ib) and (Iaa) wherein
$R^6$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;
preferably $R^6$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system;
more preferably $R^6$ represents a hydrogen atom; a linear or branched, saturated, optionally at least mono-substituted aliphatic group; an optionally at least mono-substituted aryl group;

most preferably $R^6$ represents a linear or branched, saturated, optionally at least mono-substituted $C_{1-6}$-alkyl group; an optionally at least mono-substituted phenyl group.

Another preferred embodiment of the present invention are compounds of general formula (I), (Ia), (Ib) or (Iaa) wherein
$R^1$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;
preferably $R^1$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; an branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group may be condensed with another, optionally at least mono-substituted mono- or polycyclic ring system;
more preferably $R^1$ represents a hydrogen atom; a linear or branched, saturated, optionally at least mono-substituted aliphatic group; an optionally at least mono-substituted aryl group; an optionally at least mono-substituted alkyl-aryl group; an optionally at least mono-substituted alkyl-heterocyclyl group;
most preferably $R^1$ represents a linear or branched, saturated, optionally at least mono-substituted $C_{1-4}$-alkyl group; an optionally at least mono-substituted phenyl group; an optionally at least mono-substituted benzyl group; an optionally at least mono-substituted $CH_2$-heterocyclyl group.

Another preferred embodiment of the present invention are compounds of general formula (I), (Ia), (Ib) and (Iaa) wherein
$R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;
preferably $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system;
more preferably $R^{19}$ represents a hydrogen atom; a linear or branched, saturated, optionally at least mono-substituted aliphatic group; an unbranched or branched, saturated or unsaturated, optionally at least mono-substituted alkoxy radical; an optionally at least mono-substituted aryl group;
most preferably $R^{19}$ represents a linear or branched, saturated, optionally at least mono-substituted $C_{1-4}$-alkyl group; an optionally at least mono-substituted phenyl group.

A highly preferred embodiment of the present invention are compounds of general formula (Iaa)

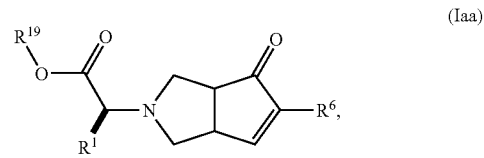

(Iaa)

wherein
$R^6$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;
preferably $R^6$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system;
more preferably $R^6$ represents a hydrogen atom; a linear or branched, saturated, optionally at least mono-substituted aliphatic group; an optionally at least mono-substituted aryl group;

most preferably R⁶ represents a linear or branched, saturated, optionally at least mono-substituted $C_{1-6}$-alkyl group; an optionally at least mono-substituted phenyl group.

and/or

R¹ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

preferably R¹ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; an branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group may be condensed with another, optionally at least mono-substituted mono- or polycyclic ring system;

more preferably R¹ represents a hydrogen atom; a linear or branched, saturated, optionally at least mono-substituted aliphatic group; an optionally at least mono-substituted aryl group; an optionally at least mono-substituted alkyl-aryl group; an optionally at least mono-substituted alkyl-heterocyclyl group;

most preferably R¹ represents a linear or branched, saturated, optionally at least mono-substituted $C_{1-6}$-alkyl group; an optionally at least mono-substituted phenyl group; an optionally at least mono-substituted benzyl group; an optionally at least mono-substituted $CH_2$-heterocyclyl group;

and/or

R¹⁹ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

preferably R¹⁹ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system;

more preferably R¹⁹ represents a hydrogen atom; a linear or branched, saturated, optionally at least mono-substituted aliphatic group; an unbranched or branched, saturated or unsaturated, optionally at least mono-substituted alkoxy radical; an optionally at least mono-substituted aryl group;

most preferably R¹⁹ represents a linear or branched, saturated, optionally at least mono-substituted $C_{1-4}$-alkyl group; an optionally at least mono-substituted phenyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Most highly preferred are compounds of general formula (I) as described above, selected from the group consisting of:

(2S)-ethyl 2-(4-oxo-5-phenyl-1,3a,4,6a-tetrahydrocyclopenta[c]pyrrol-2(1H)-yl)propanoate;

(2S)-ethyl 2-((3aR,6aS)-(4-oxo-5-phenyl-1,3a,4,6a-tetrahydrocyclopenta[c]pyrrol-2(1H)-yl)propanoate;

(2S)-ethyl 2-((3aS,6aR)-(4-oxo-5-phenyl-1,3a,4,6a-tetrahydrocyclopenta[c]pyrrol-2(1H)-yl)propanoate;

(2S)-ethyl 2-(5-butyl-4-oxo-1,3a,4,6a-tetrahydrocyclopenta[c]pyrrol-2(1H)-yl)propanoate;

(2S)-ethyl 2-((3aR,6aS)-5-butyl-4-oxo-1,3a,4,6a-tetrahydrocyclopenta[c]pyrrol-2(1H)-yl)propanoate;

(2S)-ethyl 2-((3aS,6aR)-5-butyl-4-oxo-1,3a,4,6a-tetrahydrocyclopenta[c]pyrrol-2(1H)-yl)propanoate;

(2S)-ethyl 2-(4-oxo-5-phenyl-1,3a,4,6a-tetrahydrocyclopenta[c]pyrrol-2(1H)-yl)-3-methylbutanoate;

(2S)-ethyl 2-(3aR,6aS)-4-oxo-5-phenyl-1,3a,4,6a-tetrahydrocyclopenta[c]pyrrol-2(1H)-yl)-3-methylbutanoate;

(2S)-ethyl 2-((3aS,6aR)-4-oxo-5-phenyl-1,3a,4,6a-tetrahydrocyclopenta[c]pyrrol-2(1H)-yl)-3-methylbutanoate;

(2S)-ethyl 2-(5-butyl-4-oxo-1,3a,4,6a-tetrahydrocyclopenta[c]pyrrol-2(1H)-yl)-3-methylbutanoate;

(2S)-ethyl 2-(3aR,6aS)-(5-butyl-4-oxo-1,3a,4,6a-tetrahydrocyclopenta[c]pyrrol-2(1H)-yl)-3-methylbutanoate;

(2S)-ethyl 2-(3aS,6aR)-(5-butyl-4-oxo-1,3a,4,6a-tetrahydrocyclopenta[c]pyrrol-2(1H)-yl)-3-methylbutanoate;

(2S)-methyl 4-methyl-2-(4-oxo-5-phenyl-1,3a,4,6a-tetrahydrocyclopenta[c]pyrrol-2(1H)-yl)pentanoate;

(2S)-methyl 4-methyl-2-((3aR,6aS)-4-oxo-5-phenyl-1,3a,4,6a-tetrahydrocyclopenta[c]pyrrol-2(1H)-yl)pentanoate;

(2S)-methyl 4-methyl-2-((3aS,6aR)-4-oxo-5-phenyl-1,3a,4,6a-tetrahydrocyclopenta[c]pyrrol-2(1H)-yl)pentanoate;

(2S)-methyl 2-(5-butyl-4-oxo-1,3a,4,6a-tetrahydrocyclopenta[c]pyrrol-2(1H)-yl)-4-methylpentanoate;

(2S)-methyl 2-((3aR,6aS)-(5-butyl-4-oxo-1,3a,4,6a-tetrahydrocyclopenta[c]pyrrol-2(1H)-yl)-4-methylpentanoate;

(2S)-methyl 2-((3aS,6aR)-(5-butyl-4-oxo-1,3a,4,6a-tetrahydrocyclopenta[c]pyrrol-2(1H)-yl)-4-methylpentanoate;

(2S)-methyl 2(4-oxo-5-phenyl-1,3a,4,6a-tetrahydrocyclopenta[c]pyrrol-2(1H) yl)-3-phenylpropanoate;
(2S)-methyl 2-((3aR,6aS)-(4-oxo-5-phenyl-1,3a,4,6a-tetrahydro cyclopenta[c]pyrrol-2(1H)-yl)-3-phenylpropanoate;
(2S)-methyl 2-((3aS,6aR)-(5-butyl-4-oxo-1,3a,4,6a-tetrahydrocyclopenta[c]pyrrol-2(1H)-yl)-3-phenylpropanoate;
(2S)-methyl 2-(5-butyl-4-oxo-1,3a,4,6a-tetrahydrocyclopenta[c]pyrrol-2(1H)-yl)-3-phenylpropanoate;
(2S)-methyl 2-((3aR,6aS)-(5-butyl-4-oxo-1,3a,4,6a-tetrahydrocyclopenta[c]pyrrol-2(1H)-yl)-3-phenylpropanoate;
(2S)-methyl 2-((3aS,6aR)-(5-butyl-4-oxo-1,3a,4,6a-tetrahydrocyclopenta[c]pyrrol-2(1H)-yl)-3-phenylpropanoate;
(2S)-methyl 2-(4-oxo-5-phenyl-1,3a,4,6a-tetrahydrocyclopenta[c]pyrrol-2(1H)-yl)-2-phenylacetate;
(2S)-methyl 2-((3aR,6aS)-(4-oxo-5-phenyl-1,3a,4,6a-tetrahydrocyclopenta[c]pyrrol-2(1H)-yl)-2-phenylacetate;
(2S)-methyl 2-((3aS,6aR)-(4-oxo-5-phenyl-1,3a,4,6a-tetrahydrocyclopenta[c]pyrrol-2(1H)-yl)-2-phenylacetate;
(2S)-methyl 2-(5-butyl-4-oxo-1,3a,4,6a-tetrahydrocyclopenta[c]pyrrol-2(1H)-yl)-2-phenylacetate;
(2S)-methyl 2-(3aR,6aS)-(5-butyl-4-oxo-1,3a,4,6a-tetrahydro cyclopenta[c]pyrrol-2(1H)-yl)-2-phenylacetate;
(2S)-methyl 2-((3aS,6aR)-5-butyl-4-oxo-1,3a,4,6a-tetrahydro cyclopenta[c]pyrrol-2(1H)-yl)-2-phenylacetate;
(2S)-methyl 3-1H-indol-3-yl)-2-(3a,6a-cis)-6-oxo-5-phenyl-3,3a,6,6a-tetrahydrocyclopenta[c]pyrrol-2(1H)-yl)propanoate; or
(2S)-methyl 2-((3a,6a-cis)-5-butyl-6-oxo-3,3a,6,6a-tetrahydrocyclopenta[c]pyrrol-2(1H)-yl-3-(1H-indol-3-yl)propanoate;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the present invention refers to a process for obtaining substituted bicyclic tetrahydropyrrole compounds of general formula (Ia), characterized in that at least one substituted pyrroline compound of general formula (II),

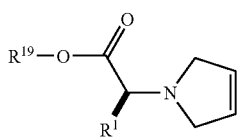

(II)

wherein $R^1$ has the meaning given above, is reacted in presence of a catalyst such as e.g. $CO_2(CO)_8$, an apolar dissolvent such as e.g. DCE (dichloroethane) and an additive (Lewis base) such as e.g. DMSO, thioanisole, cyclohexylamine, preferably DMSO at a reflux temperature between 20 and 100° C., preferably between 50 and 90° C., most preferably between 80 and 90° C., with a compound of general formula (III),

(III)

wherein Z represents a CH—$R^6$ group; a CH—CHR$^7$R$^{7a}$ group; a CH—(C=O)—R$^8$ group; a CH—$CH_2(SO_2)$—$R^9$ group; a CH—$CH_2(SO_2)$—NR$^{10}$R$^{10a}$ group; or a CH—(C=O)—NR$^{10}$R$^{10a}$ group, to give compounds of general formula (Ia),

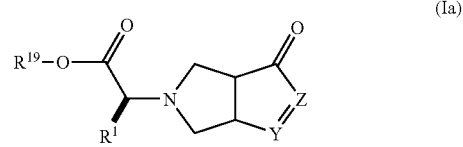

(Ia)

wherein the bond between Y and Z is unsaturated (Y=Z) in which Y represents a CH group and Z has the meaning as defined above.

A general scheme for compounds of general formula (Ia) with Y and Z forming an unsaturated bond (Y=Z) is given below in scheme (I):

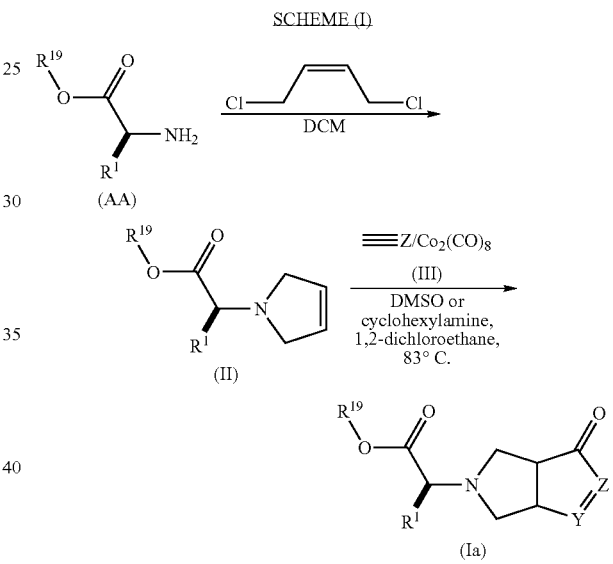

The synthesis of 1-substituted-3-pyrrolines of general formula (II) is performed by treatment of amino acid (ethyl or methyl)esters of general formula (AA) with (Z)-1,4-dichloro-2-butene in an apolar dissolvent such as e.g. dichloromethane (DCM) at a temperature between 10° and 30° Celsius, preferably at room temperature. A reaction time which worked very well for both steps of the reaction shown above was between 20 and 30 h, especially 24 h. Another condition which turned out to be preferable was the use of an excess (e.g. 3.5 eq.) of the amino acid ester (according to formula AA) preferably in the absence of any added base. Advantageously the unreacted starting material can be easily recovered and recycled, and this direct procedure takes place without the need of nitrogen basicity deactivation by strong Lewis acids. This would be preferable when racemization-prone substrates are involved in the reaction.

Compounds of general formula (I) with Y and Z forming a saturated (Y—Z) bond are obtained by performing a 1,4-addition reaction with a compound of general formula (Ia),

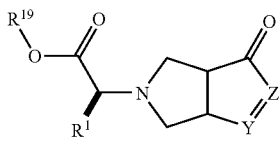

(Ia)

wherein R¹ has the meaning as described above, Z represents a CH—R⁶ group; a CH—CHR⁷R⁷ᵃ group; a CH—(C=O)—R⁸ group; a CH—CH₂(SO₂)—R⁹ group; a CH—CH₂(SO₂)—NR¹⁰R¹⁰ᵃ group; or a CH—(C=O)—NR¹⁰R¹⁰ᵃ group and Y represents a CH group, to give a compound of general formula (Ib),

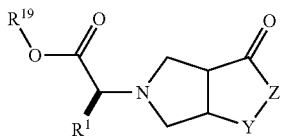

(Ib)

wherein R¹ has the meaning as defined above, Y and Z, as defined above, form a saturated (Y—Z) bond, and Y represents a CH₂ group; a C—R¹¹R¹² group; a CH—(C=O)—R¹⁶ group; a CH—(SO₂)—R¹⁷ group; CH—(SO₂)—NR¹⁸R¹⁸ᵃ group; or a CH—(C=O)—NR¹⁸R¹⁸ᵃ group.

The performance of said 1,4-addition reaction is well known by those skilled in the art and is preferably done in the presence of a catalyst such as Copper iodide and an apolar substrate such as e.g. Et₂O. The reactants in this 1,4-addition may be metallic or non-metallic. Preferably, the reactants are metallic.

Preferred examples of metallic reactants are Y—Li and Y—Mg$_x$, wherein Y represents a CH₂ group; a C—R¹¹R¹² group; a CH—(C=O)—R¹⁶ group; a CH—(SO₂)—R¹⁷ group; CH—(SO₂)—NR¹⁸R¹⁸ᵃ group; or a CH—(C=O)—NR¹⁸R¹⁸ᵃ group; and x refers to the valency of Mg, depending on the ligand Y.

A general scheme for compounds of general formula (Ib) with Y and Z forming a saturated bond (Y—Z) is given below in scheme (II):

SCHEME (II)

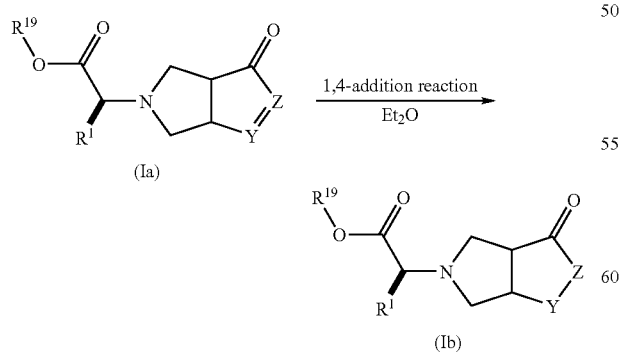

Synthesis of Intermediates/Compounds of Formula II:

As described in Scheme I above, the Intermediate/compound (a 1-substituted-3-pyrrolin) of general formula (II)

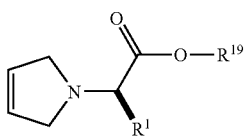

is synthesized by treatment of an amino acid (ethyl or methyl) esters of general formula (M) with R¹ and R¹⁹ as defined above

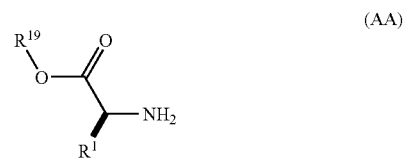

(AA)

with (Z)-1,4-dichloro-2-butene in an apolar dissolvent such as e.g. dichloromethane (DCM) at a temperature between 100 and 300 Celsius, preferably at room temperature. Preferably in presence or absence of an additional organic or inorganic base. A reaction time which worked very well was between 20 and 30 h, especially 24 h. Another condition which turned out to be preferable was the use of an excess (e.g. 3.5 eq.) of the amino acid ester (according to formula AA) preferably in the absence of any added base. Advantageously the unreacted starting material can be easily recovered and recycled, and this direct procedure takes place without the need of nitrogen basicity deactivation by strong Lewis acids. This would be preferable when racemization-prone substrates are involved in the reaction.

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution.

Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

It has been found that the compounds of general formula (I) and given below, stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

The compounds of general formula (I) given below, their stereoisomers, corresponding salts thereof and corresponding solvates are toxicologically acceptable and are therefore suitable as pharmaceutical active substances for the preparation of medicaments.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of the present invention relates to a medicament comprising at least one compound of general formula (I), optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

In an alternative embodiment of the present invention, the medicament comprises at least one compound of general formula (I), said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the invention is a medicament comprising at least one combination of compounds according to the invention and optionally one or more pharmaceutically acceptable excipients.

In an embodiment according to the invention the medicament is for the prophylaxis and/or treatment of Alzheimer's disease.

In an embodiment according to the invention the medicament is for the prophylaxis and/or treatment of one or more disorders selected from the group consisting of Said medicament may also comprise any combination of one or more of the compounds of general formula (I) given above, stereoisomers thereof, physiologically acceptable salts thereof or physiologically acceptable solvates thereof.

Another aspect of the present invention is the use of at least one compound of general formula (I) given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients, for the preparation of a medicament for the modulation of sigma receptors, preferably for the prophylaxis and/or treatment of Alzheimer's disease.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating.

The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Another aspect of the present invention refers to a method for the prophylaxis and/or treatment of Alzheimer's disease, the method comprising administering to the subject at least one compound of general formula (I) as described above and optionally at least one further active substance and/or optionally at least one auxiliary substance to the subject.

Another aspect of the present invention refers to the use of a compound of general formula (I) in the manufacture of a medicament.

Another aspect of the present invention refers to the use of a compound of general formula (I) in the manufacture of a medicament for the treatment or prophylaxis of a sigma receptor-mediated disease or condition.

Another aspect of the present invention refers to the use mentioned above of a compound of general formula (I) wherein the sigma receptor-mediated disease or condition is Alzheimer's disease.

Another aspect of the present invention refers to the use mentioned above of a compound of general formula (I) wherein the sigma receptor-mediated disease or condition is diarrhoea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety, psychosis or schizophrenia; inflammation, or autoimmune diseases.

Another aspect of the present invention refers to the use mentioned above of a compound of general formula (I) wherein the sigma receptor-mediated disease or condition is a disorder selected from the group consisting of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

Another aspect of the present invention refers to the use mentioned above of a compound of general formula (I) wherein the sigma receptor-mediated disease or condition is a disorder selected from the group consisting of pain, preferably neuropathic pain, inflammatory pain or other pain conditions involving allodynia and/or hyperalgesia.

Another aspect of the present invention refers to the use of a compound of general formula (I) as a pharmacological tool.

In a separate aspect the invention also encompasses the intermediates/compound of general formula (II),

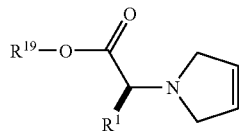

wherein
- $R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system; an optionally, at least mono-substituted benzhydryl group;
- $R^{19}$ represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As said these compounds are useful intermediates for the synthesis of pharmacological interesting compounds.

In a preferred embodiment the compound of formula II is characterized in that
- $R^1$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;
- preferably $R^1$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; an branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group may be condensed with another, optionally at least mono-substituted mono- or polycyclic ring system;
- more preferably $R^1$ represents a hydrogen atom; a linear or branched, saturated, optionally at least mono-substituted aliphatic group; an optionally at least mono-substituted aryl group; an optionally at least mono-substituted alkyl-aryl group; an optionally at least mono-substituted alkyl-heterocyclyl group;
- most preferably $R^1$ represents a linear or branched, saturated, optionally at least mono-substituted $C_{1-6}$-alkyl group; an optionally at least mono-substituted phenyl group; an optionally at least mono-substituted benzyl group; an optionally at least mono-substituted $CH_2$-heterocyclyl group;

and/or
- $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

preferably $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system;

more preferably $R^{19}$ represents a hydrogen atom; a linear or branched, saturated, optionally at least mono-substituted aliphatic group; an unbranched or branched, saturated or unsaturated, optionally at least mono-substituted alkoxy radical; an optionally at least mono-substituted aryl group;

most preferably $R^{19}$ represents a linear or branched, saturated, optionally at least mono-substituted $C_{1-4}$-alkyl group; an optionally at least mono-substituted phenyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment the compound of formula II is selected from the group consisting of:
2-(2,5-Dihydro-pyrrol-1-yl)-propionic acid ethyl ester,
2-(2,5-Dihydro-pyrrol-1-yl)-3-methyl-butyric acid ethyl ester,
2-(2,5-Dihydro-pyrrol-1-yl)-4-methyl-pentanoic acid methyl ester,
2-(2,5-Dihydro-pyrrol-1-yl)-3-phenyl-propionic acid methyl ester,
(2,5-Dihydro-pyrrol-1-yl)-phenyl-acetic acid methyl ester,
2-(2,5-Dihydro-pyrrol-1-yl)-3-(1H-indol-3-yl)-propionic acid methyl ester,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof The compounds according to formula II are also of physiological interest, seeming to have affinity to the Sigma receptor and/or to have an activity in the treatment of Alzheimer's disease.

Another preferred aspect of the invention is a medicament comprising at least one compound of general formula (II), according to the invention, said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

Another preferred aspect of the invention is the use of a compound of general formula (II) according to the invention in the manufacture of a medicament.

Another preferred aspect of the invention is the use of a compound of general formula (II) according to the invention in the manufacture of a medicament for the treatment or prophylaxis of a sigma receptor-mediated disease or condition.

In another preferred embodiment of the invention the use of the compound of general formula (II) according to the invention is characterized in that the sigma receptor-mediated disease or condition is Alzheimer's disease.

In another preferred embodiment of the invention the use of the compound of general formula (II) according to the invention is characterized in that the sigma receptor-mediated disease or condition is selected from diarrhoea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety, psychosis or schizophrenia; inflammation, or autoimmune diseases; or is elevated trigyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia, or is pain, preferably neuropathic pain, inflammatory pain or other pain conditions involving allodynia and/or hyperalgesia.

The present invention is illustrated below with the aid of examples. These illustrations are given solely by way of example and do not limit the general spirit of the present invention.

EXAMPLES

General Procedure for the synthesis of the intermediates: A mixture of cis-1,4-dichloro-2-butene (1 eq) and aminoester 1a-f (3.5 eq) in dichloromethane was stirred at r.t. for 24 hours. Dichloromethane was added and the precipitated was filtered. The filtrate was washed with water and sat. solution of NaCl, dried over $Na_2SO_4$, filtered and concentrated. The crude was purified by flash chromatography.

(S)-ethyl 2-(2H-pyrrol-1(5H)-yl)propanoate

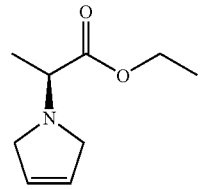

From L-alanine ethyl ester (383 mg, 3.2 mmol), dichloromethane (0.1 ml) and cis-1,4-dichloro-2-butene (140 mg, 1.0 mmol). Flash chromatography: silica gel, gradient neat hexane to hexane:ethyl acetate (1:2) afforded the product (96 mg, 52%) as yellow oil.
$^1$H NMR (400 MHz, CDCl3): δ (ppm) 5.76 (s, 2H), 4.17 (q, J=7 Hz, 2H), 3.63 (m, 4H), 3.46 (q, J=7 Hz, 1H), 1.36 (d, J=7

Hz, 3H), 1.26 (t, J=7 Hz, 3H). $^{13}$C NMR (75 MHz, CDCl$_3$): δ (ppm) 173.86, 127.13, 60.35, 60.28, 56.55, 17.22, 14.26. MS (EI+) m/z: 170.1 (M+H$^+$).

(S)-ethyl 3-methyl-2-(2H-pyrrol-1(5H)-yl)butanoate

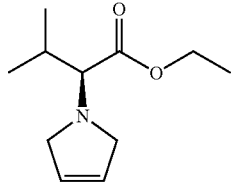

From L-valine ethyl ester (1.0 g, 6.9 mmol), dichloromethane (1 ml) and cis-1,4-dichloro-2-butene (250 mg, 2.0 mmol). Flash chromatography: silica gel, gradient neat hexane to hexane:ethyl acetate (1:2) afforded the product (205 mg, 52%) as yellow oil.

$^1$H NMR (400 MHz, CDCl3): δ (ppm) 5.75 (s, 2H), 4.10 (q, J=7 Hz, 2H), 3.70 (m, 2H), 3.51 (m, 2H), 2.98 (d, J=7 Hz, 1H), 1.95 (m, 1H), 1.20 (t, J=7 Hz, 3H), 0.96 (d, J=7 Hz, 3H), 0.86 (d, J=7 Hz, 3H). $^{13}$C NMR (75 MHz, CDCl$_3$) δ (ppm) 172.67, 127.08, 70.72, 59.70, 55.79, 29.16, 19.94, 19.07, 14.45. MS (EI+) m/z: 198.1 (M+H$^+$).

(S)-methyl 4-methyl-2-(2H-pyrrol-1(5H)-yl)pentanoate

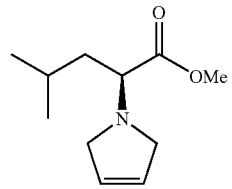

From L-leucine methyl ester (520 mg, 3.56 mmol), dichloromethane (1 ml) and cis-1,4-dichloro-2-butene (135 mg, 1.08 mmol). Flash chromatography: silica gel, gradient hexane:ethyl acetate (3:1 to 1:1) afforded the product (180 mg, 84%) as yellow oil.

$^1$H NMR (400 MHz, CDCl3): δ (ppm) 5.73 (s, 2H), 3.70 (m, 2H), 3.66 (s, 3H), 3.59-3.54 (m, 2H), 3.47 (m, 1H), 1.62 (m, 2H), 1.53 (m, 1H), 0.90 (m, 6H). $^{13}$C NMR (75 MHz, CDCl$_3$) δ (ppm) 174.25, 127.15, 62.11, 56.07, 51.24, 40.37, 24.84, 22.77. HRMS (ES+) 198.1501, calculated for C$_{11}$H$_{19}$NO$_2$+H$^+$: 198.1494.

(S)-methyl 3-phenyl-2-(2H-pyrrol-1(5H)-yl)propanoate

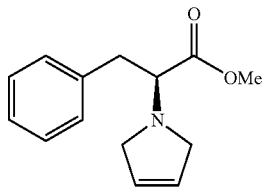

From L-phenylalanine methyl ester (365 mg, 2.04 mmol), dichloromethane (4 ml) and cis-1,4-dichloro-2-butene (71 mg, 0.58 mmol). Flash chromatography: silica gel, hexane:ethyl acetate (2:1) afforded the product (83 mg, 62%) as colourless oil.

$^1$H NMR (400 MHz, CDCl3): δ (ppm) 7.30-7.17 (m, 5H), 5.76 (s, 2H), 3.75 (m, 2H), 3.67 (m, 3H), 3.59 (s, 3H), 3.05 (m, 2H). $^{13}$C NMR (75 MHz, CDCl$_3$) δ (ppm) 172.93, 138.12, 129.27, 128.41, 127.27, 126.56, 66.63, 56.36, 51.22, 37.67. MS (EI+) m/z: 232.1 (M+H)$^+$.

(S)-methyl 2-phenyl-2-(2H-pyrrol-1(5H)-yl)acetate

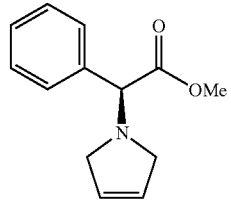

From L-phenylglycine methyl ester (808 mg, 4.89 mmol), dichloromethane (0.1 ml) and cis-1,4-dichloro-2-butene (170 mg, 1.39 mmol). Flash chromatography: silica gel, gradient neat hexane to hexane:ethyl acetate (1:2) afforded the product (197 mg, 65%) as colourless oil.

$^1$H NMR (400 MHz, CDCl3): δ (ppm) 7.48 (m, 2H), 7.34 (m, 3H), 5.75 (s, 2H), 4.32 (s, 1H), 3.69 (s, 3H), 3.54 (m, 2H), 3.52 (m, 2H). $^{13}$C NMR (75 MHz, CDCl$_3$): δ (ppm) 172.23, 137.31, 128.65, 128.52, 128.33, 127.20, 72.56, 58.09, 52.09. MS (EI+) m/z: 218.1 (M+H)$^+$.

(S)-methyl 3-(1H-indol-3-yl)-2-(2H-pyrrol-1(5H)-yl)propanoate

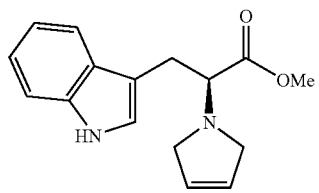

From L-tryptophan methyl ester (432 mg, 1.98 mmol), dichloromethane (1 ml) and cis-1,4-dichloro-2-butene (77 mg, 0.62 mmol). Flash chromatography: silica gel hexane:ethyl acetate (1:1) afforded the product (123 mg, 73%) as yellow oil.

$^1$H NMR (400 MHz, CDCl3): δ (ppm) 8.35 (bs, 1H), 7.62 (d, J=7.5 Hz, 1H), 7.29 (d, J=7.5 Hz, 1H), 7.14 (m, 2H), 7.00 (d, J=2.5 Hz, 1H), 5.81 (s, 2H), 3.83 (m, 3H), 3.74 (m, 2H), 3.59 (s, 3H), 3.353.16 (m, 2H). $^{13}$C NMR (75 MHz, CDCl$_3$) δ (ppm) 173.29, 136.08, 127.31, 127.12, 122.64, 121.76, 119.15, 118.44, 111.41, 111.16, 65.93, 56.41, 51.29, 27.20. HRMS (ES+) 271.1439, calculated for C$_{16}$H$_{18}$N$_2$O$_2$+H$^+$: 271.1447.

General Procedure for the synthesis of Pauson-Khand adducts: A mixture of alkyne (1.2 eq) and CO$_2$(CO)$_8$ (1.3 eq) in 1,2-dichloroethane was stirred at r.t. for 2 hours. A solution of pyrroline (1 eq) in 1,2-dichloroethane and the additive (dimethylsulphoxide or cyclohexylamine, 3.5 eq) was added, and the mixture was heated at 83° C. for 24 hours. The reaction mixture was cooled at r.t. and filtrated through celite and washed with dichloromethane. The filtrate was concentrated and purified by flash chromatography.

The following examples were synthesized according to the general Schemes and descriptions given above and their structure was determined by $^1$H-NMR and MS.

Examples 11 and 12

(2S)-ethyl 2-(4-oxo-5-phenyl-1,3a,4,6a-tetrahydro-cyclopenta[c]pyrrol-2(1H)-yl)propanoate (3ap)

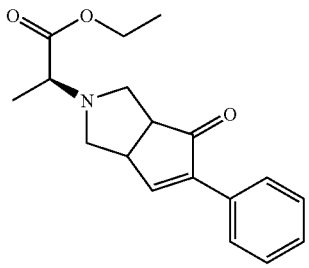

From phenylacetylene (61 mg, 0.58 mmol), $CO_2CO_8$ (200 mg, 0.58 mmol), (S)-ethyl 2-(2H-pyrrol-1(5H)-yl)propanoate (90 mg, 0.53 mmol), dimethylsulphoxide (145 mg, 1.86 mmol) and 1,2-dichloroethane (3 ml). Flash chromatography: silica gel, gradient neat hexane to hexane:ethyl acetate (1:2), afforded the product (30 mg, 18%) as yellow oil. Mixture of two diastereomers. Purification by HPLC: Chiralcel OD-H 1 cm diam.×25 cm. n-Hexane:2-propanol (90:10), 4.3 ml/min.

Example 11

(2S)-ethyl 2-((3aR,6aS)-(4-oxo-5-phenyl-1,3a,4,6a-tetrahydrocyclopenta[c]pyrrol-2(1H)-yl)propanoate

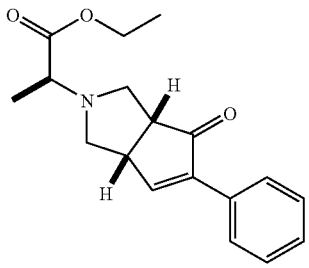

$^1$H NMR (400 MHz, CDCl3): δ (ppm) 7.72 (m, 2H), 7.68 (d, J=3 Hz, 1H), 7.40-7.29 (m, 3H), 4.14 (q, J=7 Hz, 2H), 3.38 (m, 1H), 3.27 (q, J=7 Hz, 1H), 3.17 (m, 1H), 2.94 (m, 1H), 2.98 (m, 1H), 2.75 (q, J=8 Hz, 2H), 1.27 (d, J=7 Hz, 3H), 1.26 (t, J=7 Hz, 3H). HPLC: chiralcel OD-H 0.46 cm diam.×25 cm. n-Hexane:2-propanol (90:10), 0.5 ml/min, 254 nm. R.T. 9.2 min. HRMS (ES+) 300.1600, calculated for $C_{18}H_{21}NO_3$+H$^+$: 300.1600. $[α]^{20}_D$+37.8° (c=1, CHCl$_3$).

Example 12

(2S)-ethyl 2-((3aS,6aR)-(4-oxo-5-phenyl-1,3a,4,6a-tetrahydrocyclopenta[c]pyrrol-2(1H)-yl)propanoate

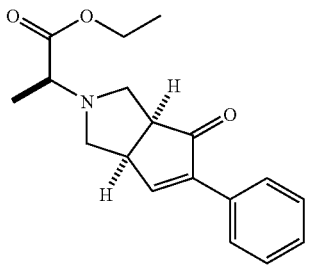

$^1$H NMR (400 MHz, CDCl3): δ (ppm) 7.73 (m, 2H), 7.69 (d, J=3 Hz, 1H), 7.40-7.29 (m, 3H), 4.15 (q, J=7 Hz, 2H), 3.39 (m, 1H), 3.29 (q, J=7 Hz, 1H), 3.18 (m, 1H), 2.96 (m, 1H), 2.83 (m, 3H), 1.27 (d, J=7 Hz, 3H), 1.26 (t, J=7 Hz, 3H). HPLC: chiralcel OD-H 0.46 cm diam.×25 cm. n-Hexane:2-propanol (90:10), 0.5 ml/min, 254 nm. R.T. 11.5 min. HRMS (ES+) 300.1605, calculated for $C_{18}H_{21}NO_3$+H$^+$: 300.1600. $[α]^{20}_D$−23.8° (c=1, CHCl$_3$).

Examples 13 and 14

(2S)-ethyl 2-(5-butyl-4-oxo-1,3a,4,6a-tetrahydrocyclopenta[c]pyrrol-2(1H)-yl)propanoate

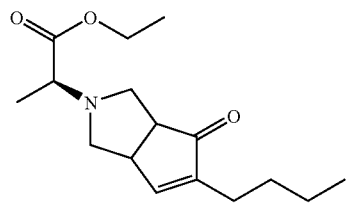

From 1-hexyne (46 mg, 0.54 mmol), $CO_2CO_8$ (203 mg, 0.59 mmol), (S)-ethyl 2-(2H-pyrrol-1(5H)-yl)propanoate (56 mg 0.33 mmol), dimethylsulphoxide (126 mg, 1.62 mmol) and 1,2-dichloroethane (3 ml). Flash chromatography: silica gel, gradient neat hexane to hexane:ethyl acetate (3:1) afforded the product (43 mg, 46%) as yellow oil. Mixture of two diastereomers. Purification by HPLC: Chiralcel OD-H 1 cm diam.×25 cm. n-Hexane:2-propanol (99.5:0.5), 5 ml/min.

Example 13

(2S)-ethyl2-((3aR,6aS)-5-butyl oxo-1,3a,4,6a-tetrahydrocyclopenta[c]pyrrol-2(1H)-yl)propanoate

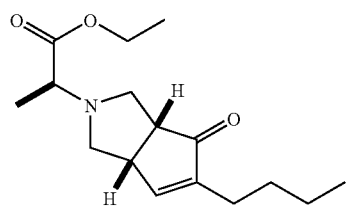

$^1$H NMR (400 MHz, CDCl3): δ (ppm) 7.12 (m, 1H), 4.14 (q. J=7 Hz, 2H), 3.26 (m, 1H), 3.22 (m, 1H), 3.06 (d, J=9 Hz, 1H), 2.76 (m, 2H), 2.66 (m, 2H), 2.16 (m, 2H), 1.45 (m, 2H), 1.32 (m, 2H), 1.26 (d, J=7 Hz, 3H) 1.25 (t, J=7 Hz, 3H), 0.89 (t, J=7 Hz, 3H). HPLC: chiralcel OD-H 0.46 cm diam.×25 cm. n-Hexane:2-propanol (99.5:0.5), 0.5 ml/min, 254 nm. R.T. 14.46 min. HRMS (ES+) 280.1906, calculated for $C_{16}H_{26}NO_3$+H$^+$: 280.1913. $[α]^{20}_D$+70.5° (c=1, CHCl$_3$).

Example 14

(2S)-ethyl 2-((3aS,6aR)-5-butyl-4-oxo-1,3a,4,6a-tetrahydrocyclopenta[c]pyrrol-2(1H)-yl)propanoate

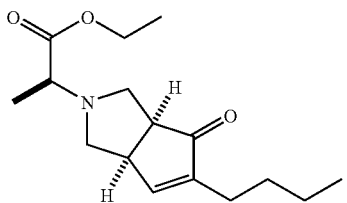

$^1$H NMR (400 MHz, CDCl$_3$): δ (ppm) 7.13 (m, 1H), 4.14 (q, J=7 Hz, 2H), 3.26 (m, 2H), 3.04 (m, 1H), 2.78 (m, 2H), 2.72 (m, 2H), 2.16 (m, 2H), 1.45 (m, 2H), 1.33 (m, 2H), 1.27 (d, J=7 Hz, 3H), 1.25 (t, J=7 Hz, 3H), 0.89 (t, J=7 Hz, 3H). HPLC: chiralcel OD-H 0.46 cm diam.×25 cm. n-Hexane:2-propanol (99.5:0.5), 0.5 ml/min, 254 nm. R.T. 15.80 min. HRMS (ES+) 280.1906, calculated for C$_{16}$H$_{26}$NO$_3$+H$^+$: 280.1913. [α]$^{20}_D$–83.6° (c=1, CHCl$_3$).

Examples 15 and 16

(2S)-ethyl 2-(4-oxo-5-phenyl-1,3a,4,6a-tetrahydrocyclopenta[c]pyrrol-2(1H)-yl)-3-methylbutanoate

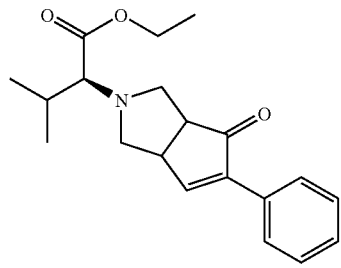

From phenylacetylene (57 mg, 0.55 mmol), CO$_2$CO$_8$ (191 mg, 0.55 mmol), (S)-ethyl 3-methyl-2-(2H-pyrrol-1(5H)-yl)butanoate (100 mg, 0.50 mmol), dimethylsulphoxide (138 mg, 1.77 mmol) and 1,2-dichloroethane (2.5 ml). Flash chromatography: silica gel, gradient neat hexane to hexane:ethyl acetate (1:2) afforded the product (32 mg, 20%) as yellow oil. Mixture of two diastereomers. Purification by HPLC: Chiralcel OD-H 1 cm diam.×25 cm. n-Hexane:2-propanol (97:3). 5 ml/min.

Example 15

(2S)-ethyl 2-((3aR,6aS)-(4-oxo-5-phenyl-1,3a,4,6a-tetrahydrocyclopenta[c]pyrrol-2(1H)-yl)-3-methylbutanoate

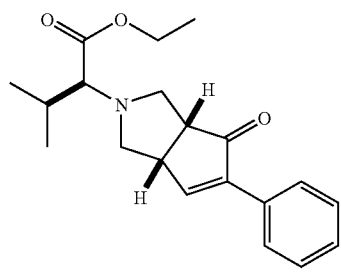

$^1$H NMR (400 MHz, CDCl3): δ (ppm) 7.65 (m, 3H), 7.40-7.30 (m, 3H), 4.17 (m, 2H), 3.34 (m, 1H), 3.15 (d, J=9 Hz, 1H), 2.90-2.82 (m, 3H), 2.76-2.64 (m, 2H), 1.98-1.88 (m, 1H), 1.28 (t, J=7 Hz, 3H), 0.82 (d, J=6.5 Hz, 3H) 0.78 (d, J=6.5 Hz, 3H). HPLC: chiralcel OD-H 0.46 cm diam.×25 cm. n-Hexane:2-propanol (97:3), 0.5 ml/min, 254 nm. R.T. 10.6 min. HRMS (ES+) 328.1926, calculated for C$_{20}$H$_{25}$NO$_3$+H$^+$: 328.1913. [α]$^{20}_D$–0.4° (c=1, CHCl$_3$).

Example 16

(2S)-ethyl 2-((3aS,6aR)-(4-oxo-5-phenyl-1,3a,4,6a-tetrahydrocyclopenta[c]pyrrol-2(1H)-yl)-3-methylbutanoate

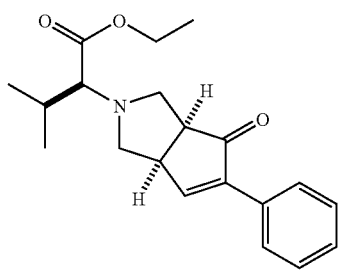

$^1$H NMR (400 MHz, CDCl3): δ (ppm) 7.66 (m, 3H), 7.41-7.30 (m, 3H), 4.17 (q, J=7 Hz, 2H), 3.31 (m, 1H), 3.21 (d, J=9 Hz, 1H), 2.90-2.73 (m, 4H), 2.68 (m, 1H), 2.04-1.94 (m, 1H), 1.28 (t, J=7 Hz, 3H), 0.83 (d, J=6.5 Hz, 3H) 0.80 (d, J=6.5 Hz, 3H). HPLC: chiralcel OD-H 0.46 cm diam.×25 cm. n-Hexane:2-propanol (97:3), 0.5 ml/min, 254 nm. R.T. 14.0 min. HRMS (ES+) 328.1923, calculated for C$_{20}$H$_{25}$NO$_3$+H$^+$: 328.1913. [α]$^{20}_D$–28.3° (c=1, CHCl$_3$).

Examples 17 and 18

(2S)-ethyl 2-(5-butyl 4-oxo-1,3a,4,6a-tetrahydrocyclopenta[c]pyrrol-2(1H)-yl)-3-methylbutanoate

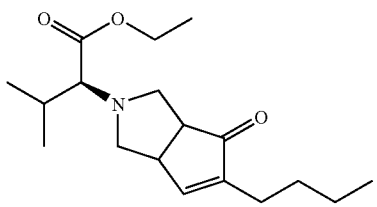

From 1-hexyne (43 mg, 0.50 mmol), CO$_2$CO$_8$ (191 mg, 0.55 mmol), (S)-ethyl 3-methyl-2-(2H-pyrrol-1(5H)-yl)butanoate (100 mg, 0.50 mmol), dimethylsulphoxide (138 mg, 1.77 mmol) and 1,2-dichloroethane (2.5 ml). Flash chromatography: silica gel, gradient neat hexane to hexane:ethyl acetate (1:2) afforded the product (45 mg, 27%) as yellow oil. Mixture of two diastereomers. Purification by HPLC: Chiralcel OD-H 1 cm diam.×25 cm. n-Hexane:2-propanol (99.5:0.5), 5 m/min.

Example 17

(2S)-ethyl 2-((3aR,6aS)-(5-butyl-4-oxo-1,3a,4,6a-tetrahydrocyclopenta[c]pyrrol-2(1H)-yl)-3-methylbutanoate

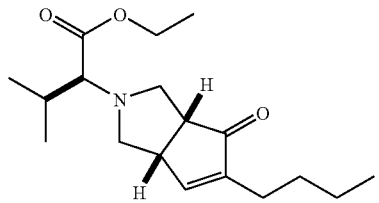

$^1$H NMR (400 MHz, CDCl3): δ (ppm) 7.12 (m, 1H), 4.16 (q, J=7 Hz, 2H), 3.20 (m, 1H), 3.05 (m, 1H), 2.86 (m, 1H), 2.70-2.60 (m, 4H), 2.16 (m, 2H), 1.92 (m, 1H), 1.43 (m, 2H), 1.32 (m, 2H), 1.27 (t, J=7 Hz, 3H), 0.88 (t, J=7 Hz, 3H), 0.82 (m, 6H). HPLC: chiralcel OD-H 0.46 cm diam.×25 cm. n-Hexane:2-propanol (99.5:0.5), 0.5 ml/min, 254 nm. R.T. 9.4 min. HRMS (ES+) 308.2228, calculated for $C_{18}H_{29}NO_3$+H$^+$: 308.2226. $[\alpha]^{20}_D$+54.4° (c=1, CHCl$_3$).

Example 18

(2S)-ethyl 2-((3aS,6aR)-(5-butyl oxo-1,3a,4,6a-tetrahydrocyclopenta[c]pyrrol-2(1H)-yl)-3-methylbutanoate

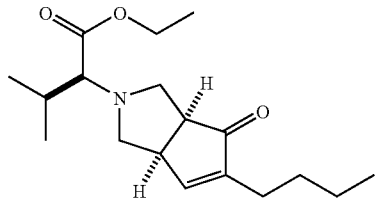

$^1$H NMR (400 MHz, CDCl3): δ (ppm) 7.13 (m, 1H), 4.15 (q, J=7 Hz, 2H), 3.17 (m, 1H), 3.06 (m, 1H), 2.81 (m, 1H), 2.67 (m, 3H), 2.59 (m, 1H), 2.16 (m, 2H), 1.96 (m, 1H), 1.43 (m, 2H), 1.32 (m, 2H), 1.27 (t, J=7 Hz, 3H), 0.88 (t, J=7 Hz, 3H), 0.82 (m, 6H). HPLC: chiralcel OD-H 0.46 cm diam.×25 cm. n-Hexane:2-propanol (99.5:0.5), 0.5 ml/min, 254 nm. R.T. 10.2 min. HRMS (ES+) 308.2228, calculated for $C_{18}H_{29}NO_3$+H$^+$: 308.2226. $[\alpha]^{20}_D$−125.4° (c=1, CHCl$_3$).

Examples 19 and 20

(2S)-methyl 4-methyl-2-(4-oxo-5-phenyl-1,3a,4,6a-tetrahydrocyclopenta[c]pyrrol-2(1H)-yl)pentanoate

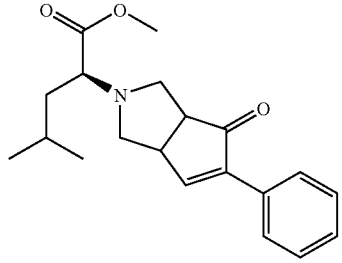

From phenylacetylene (41 mg, 0.39 mmol), CO$_2$CO$_8$ (147 mg, 0.43 mmol), (S)-methyl 4-methyl-2-2H-pyrrol-1(5H)-yl)pentanoate (71 mg, 0.36 mmol), dimethylsulphoxide (98 mg, 1.26 mmol) and 1,2-dichloroethane (2.5 ml). Flash chromatography: silica gel, dichloromethane, afforded 3c-1 (42 mg, 35%) as yellow solid. Mixture of two diastereomers. Purification by HPLC: Chiralcel OD-H 1 cm diam.×25 cm. n-Hexane:2-propanol (97:3), 5 ml/min.

Example 19

(2S)-methyl 4-methyl-2-((3aR,6aS)-4-oxo-5-phenyl-1,3a,4,6a-tetrahydrocyclopenta[c]pyrrol-2(1H)-yl)pentanoate

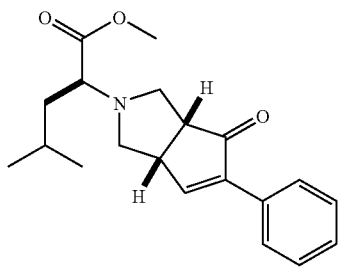

$^1$H NMR (400 MHz, CDCl3): δ (ppm) 7.67 (m, 2H), 7.65 (d, J=3 Hz, 1H), 7.40-7.31 (m, 3H), 3.68 (s, 3H), 3.38 (m, 2H), 3.16 (d, J=9 Hz, 1H), 2.89 (m, 1H), 2.84 (m, 2H), 2.77 (m, 1H), 1.58-1.42 (m, 3H), 0.85 (d, J=6.5 Hz, 3H) 0.80 (d, J=6.5 Hz, 3H). HPLC: chiralcel OD-H 0.46 cm diam.×25 cm. n-Hexane:2-propanol (99:1), 0.5 ml/min, 254 nm. R.T. 11.7 min. HRMS (ES+) 328.1923, calculated for $C_{20}H_{25}NO_3$+H$^+$: 328.1913. $[\alpha]^{20}_D$+46.1° (c=1, CHCl$_3$).

Example 20

(2S)-methyl 4-methyl-2-((3aS,6aR)-4-oxo-5-phenyl-1,3a,4,6a-tetrahydrocyclopenta[c]pyrrol-2(1H)-yl)pentanoate

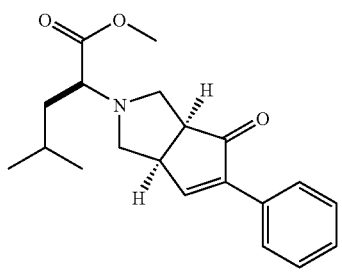

$^1$H NMR (400 MHz, CDCl3): δ (ppm) 7.70-7.65 (m, 3H), 7.40-7.30 (m, 3H), 3.68 (s, 3H), 3.37 (m, 2H), 3.18 (d, J=9 Hz, 1H), 2.92 (m, 2H), 2.82 (m, 2H), 1.59-1.44 (m, 3H), 0.86 (d, J=6.5 Hz, 3H) 0.80 (d, J=6.5 Hz, 3H). HPLC: chiralcel OD-H 0.46 cm diam.×25 cm. n-Hexane:2-propanol (99:1), 0.5 ml/min, 254 nm. R.T. 15.8 min. HRMS (ES+) 328.1922, calculated for $C_{20}H_{25}NO_3$+H$^+$: 328.1913. $[\alpha]^{20}_D$−79.2° (c=1, CHCl$_3$).

Examples 21 and 22

(2S)-methyl 2-(5-butyl-4-oxo-1,3a,4,6a-tetrahydro-cyclopenta[c]pyrrol-2(1H)-yl)-4-methylpentanoate

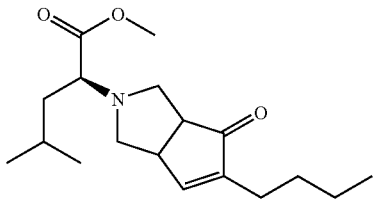

From 1-hexyne (44 mg, 0.53 mmol), $CO_2CO_8$ (194 mg, 0.56 mmol), (S)-methyl 4-methyl-2-(2H-pyrrol-1(5H)-yl)pentanoate (70 mg, 0.35 mmol), dimethylsulphoxide (97 mg, 1.25 mmol) and 1,2-dichloroethane (2.5 ml). Flash chromatography: silica gel, dichloromethane, afforded the product (37 mg, 34%) as yellow oil. Mixture of two diastereomers. Purification by HPLC: Chiralcel AS 1 cm diam.×25 cm. n-Hexane:2-propanol (99:1), 5 m/min.

Example 21

(2S)-methyl 2-((3aR,6aS)-(5-butyl-4-oxo-1,3a,4,6a-tetrahydro cyclopenta[c]pyrrol-2(1H)-yl)-4-methylpentanoate

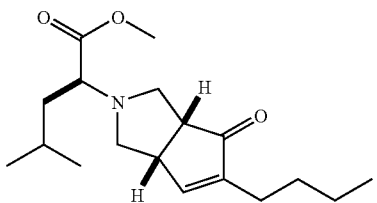

$^1$H NMR (400 MHz, $CD_3OD$): δ (ppm) 7.31 (m, 1H), 3.67 (m, 3H), 3.33 (m, 1H), 3.26 (m, 1H), 3.02 (d, J=7 Hz, 1H), 2.77 (m, 1H), 2.69 (m, 3H), 2.14 (m, 2H), 1.47 (m, 5H), 1.32 (m, 2H), 0.91 (t, J=7 Hz, 3H), 0.87 (d, J=7 Hz, 3H), 0.82 (d, J=7 Hz, 3H). HPLC: chiralcel OD-H 0.46 cm diam.×25 cm. n-Hexane:2-propanol (99:1), 0.5 m/min, 254 nm. R.T. 6.50 min. HRMS (ES+) 308.2219, calculated for $C_{18}H_{29}NO_3+H^+$: 308.2226. $[α]^{20}_D$ −140.6° (c=1, $CHCl_3$).

Example 22

(2S)-methyl 2-((3aS,6aR)-(5-butyl-4-oxo-1,3a,4,6a-tetrahydrocyclopenta[c]pyrrol-2(1H)-yl)-4-methylpentanoate

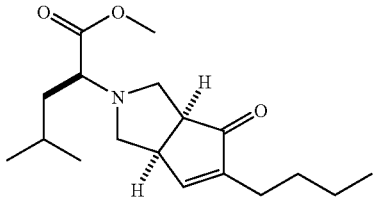

$^1$H NMR (400 MHz, $CD_3OD$): δ (ppm) 7.30 (m, 1H), 3.67 (m, 3H), 3.37 (m, 1H), 3.29 (m, 1H), 3.03 (d, J=7 Hz, 1H), 2.78 (m, 1H), 2.71 (m, 3H), 2.15 (m, 2H), 1.47 (m, 5H), 1.32 (m, 2H), 0.91 (t, J=7 Hz, 3H), 0.87 (d, J=7 Hz, 3H), 0.82 (d, J=7 Hz, 3H). HPLC: chiralcel OD-H 0.46 cm diam.×25 cm. n-Hexane:2-propanol (99:1), 0.5 ml/min, 254 nm. R.T. 7.50 min. HRMS (ES+) 308.2227, calculated for $C_{18}H_{29}NO_3+H^+$: 308.2226. $[α]^{20}_D$+78.7° (c=1, $CHCl_3$).

Examples 23 and 24

(2S)-methyl 2(4-oxo-5-phenyl-1,3a,4,6a-tetrahydro-cyclopenta[c]pyrrol-2(1H)-yl)-3-phenylpropanoate

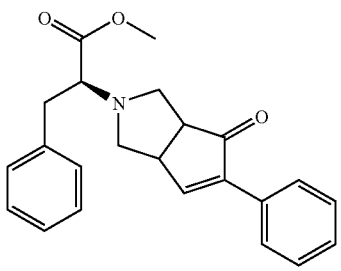

From phenylacetylene (41 mg, 0.39 mmol), $CO_2CO_8$ (147 mg, 0.43 mmol), (S)-methyl 3-phenyl-2-(2H-pyrrol-1(5H)-yl)propanoate (83 mg, 0.36 mmol), dimethylsulphoxide (98 mg, 1.26 mmol) and 1,2-dichloroethane (2.5 ml). Flash chromatography: silica gel, gradient neat dichloromethane to dichloromethane:methanol (1%) afforded the product (60 mg, 46%) as yellow oil. Mixture of two diastereomers. Purification by HPLC: Chiralcel OD-H 1 cm diam.×25 cm. n-Hexane:2-propanol (85:15), 5 ml/min.

Example 23

(2S)-methyl 2-((3aR,6aS)-(4-oxo-5-phenyl-1,3a,4,6a-tetrahydro cyclopenta[c]pyrrol-2(1H)-yl)-3-phenylpropanoate

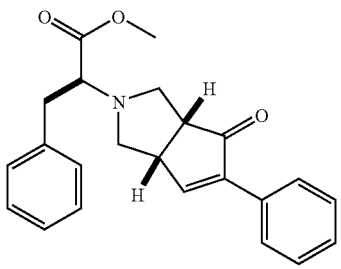

$^1$H NMR (400 MHz, $CD_3OD$): δ (ppm) 7.90 (d, J=3 Hz, 1H), 7.73 (m, 2H), 7.43-7.30 (m, 4H), 7.16 (m, 4H), 3.64 (m, 1H), 3.60 (s, 3H), 3.56 (m, 1H), 3.23 (m, 1H), 3.06 (m, 3H), 2.99 (m, 3H). HPLC: chiralcel OD-H 0.46 cm diam.×25 cm. n-Hexane:2-propanol (85:15), 0.5 ml/min, 254 nm. R.T. 11.4 min. HRMS (ES+) 362.1761, calculated for $C_{23}H_{23}NO_3+H^+$: 362.1756. $[α]^{20}_D$+11.4° (c=1, $CHCl_3$).

Example 24

(2S)-methyl 2-((3aS,6aR)-(5-butyl-4-oxo-1,3a,4,6a-tetrahydrocyclopenta[c]pyrrol-2(1H)-yl)-3-phenyl-propanoate

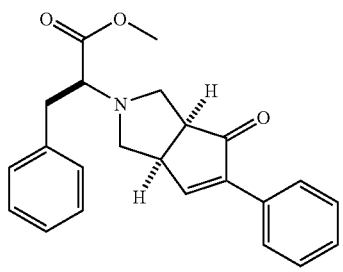

$^{1}$H NMR (400 MHz, CD$_3$OD): δ (ppm) 7.86 (d, J=3 Hz, 1H), 7.73 (m, 2H), 7.43-7.30 (m, 4H), 7.13 (m, 4H), 3.62 (s, 3H), 3.60 (m, 1H), 3.47 (m, 1H), 3.36 (m, 2H), 3.00 (m, 3H), 2.88 (m, 2H). HPLC: chiralcel OD-H 0.46 cm diam.×25 cm. n-Hexane:2-propanol (85:15), 0.5 ml/min, 254 nm. HRMS (ES+) 362.1764, calculated for C$_{23}$H$_{23}$NO$_3$+H$^+$: 362.1756. [α]$^{20}_D$ −69.7° (c=1, CHCl$_3$).

Examples 25 and 26

(2S)-methyl 2-(5-butyl-4-oxo-1,3a,4,6a-tetrahydro-cyclopenta[c]pyrrol-2(1H)-yl)-3-phenylpropanoate

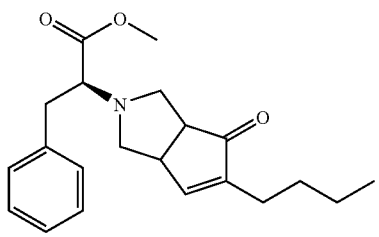

From 1-hexyne (37 mg, 0.44 mmol), CO$_2$CO$_8$ (162 mg, 0.48 mmol), (S)-methyl 3-phenyl-2-(2H-pyrrol-1(5H)-yl)propanoate (100 mg, 0.43 mmol), dimethylsulphoxide (119 mg, 1.5 mmol) and 1,2-dichloroethane (2.5 ml). Flash chromatography: silica gel, gradient neat hexane to hexane:ethyl acetate (1:1) afforded the product (70 mg, 47%) as yellow oil. Mixture of two diastereomers. Purification by HPLC: Chiralcel OD-H 1 cm diam.×25 cm. n-Hexane:2-propanol (99:1), 5 ml/min.

Example 25

(2S)-methyl 2-((3aR,6aS)-(5-butyl-4-oxo-1,3a,4,6a-tetrahydrocyclopenta[c]pyrrol-2(1H)-yl)-3-phenyl-propanoate

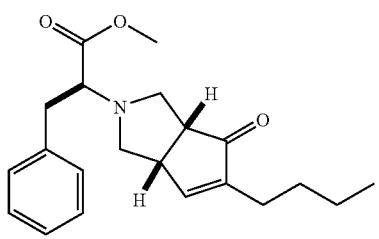

$^{1}$H NMR (400 MHz, CD$_3$OD): δ (ppm) 7.28 (m, 1H), 7.25-7.10 (m, 5H), 3.57 (m, 1H), 3.56 (s, 3H), 3.33 (m, 1H), 3.11 (d, J=7 Hz, 1H), 2.95 (m, 3H), 2.75 (m, 2H), 2.72 (m, 1H), 2.12 (m, 2H), 1.44 (m, 2H), 1.34 (m, 2H), 0.94 (t, J=7 Hz, 3H). HPLC: chiralcel OD-H 0.46 cm diam.×25 cm. n-Hexane:2-propanol (99:1), 0.5 ml/min, 254 nm. R.T. 12.7 min. HRMS (ES+) 342.2072, calculated for C$_{21}$H$_{27}$NO$_3$+H$^+$: 342.2069. [α]$^{20}_D$ +92.1° (c=1, CHCl$_3$).

Example 26

(2S)-methyl 2-((3aS,6aR)-(5-butyl-4-oxo-1,3a,4,6a-tetrahydrocyclopenta[c]pyrrol-2(1H)-yl)-3-phenyl-propanoate

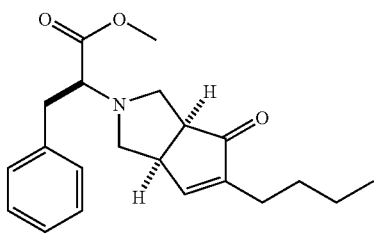

$^{1}$H NMR (400 MHz, CD$_3$OD): δ (ppm) 7.28 (m, 1H), 7.26-7.15 (m, 5H), 3.65 (m, 1H), 3.57 (s, 3H), 3.39 (m. 1H), 3.27 (m, 1H), 3.07-2.85 (m, 6H), 2.14 (m, 2H), 1.45 (m, 2H), 1.34 (m, 2H), 0.93 (t, J=7 Hz, 3H). HPLC: chiralcel OD-H 0.46 cm diam.×25 cm. n-Hexane:2-propanol (99:1), 0.5 ml/min, 254 nm. R.T. 15.0. HRMS (ES+) 342.2074, calculated for C$_{21}$H$_{27}$NO$_3$+H$^+$: 342.2069. [α]$^{20}_D$ −56.2° (c=1, CHCl$_3$).

Examples 3 and 4

(2S)-methyl 2-(4-oxo-5-phenyl-1,3a,4,6a-tetrahydro-cyclopenta[c]pyrrol-2(1H)-yl)-2-phenylacetate

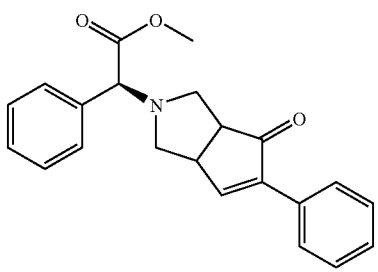

From phenylacetylene (40 mg, 0.38 mmol), CO$_2$CO$_8$ (143 mg, 0.42 mmol), (S)-methyl 2-phenyl-2-(2H-pyrrol-1(5H)-yl)acetate (70 mg, 0.32 mmol), dimethylsulphoxide (88 mg, 1.12 mmol) and 1,2-dichloroethane (2.5 ml). Flash chromatography: silica gel, hexane:ethyl acetate (2:1) afforded the product (39 mg, 35%) as yellow oil. Mixture of two diastereomers. Purification by HPLC: Chiralcel OD-H 1 cm diam.× 25 cm. n-Hexane:2-propanol (85:15), 5 ml/min.

Example 3

(2S)-methyl 2-((3aR,6aS)-(4-oxo-5-phenyl-1,3a,4,6a-tetrahydrocyclopenta[c]pyrrol-2(1H)-yl)-2-phenylacetate

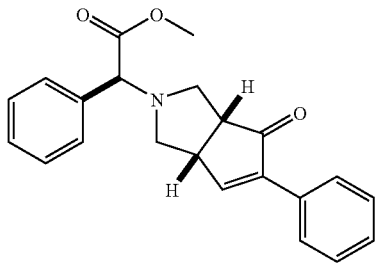

$^1$H NMR (400 MHz, CDCl3): δ (ppm) 7.73 (m, 2H), 7.69 (d, J=3 Hz, 1H), 7.42-7.26 (m, 8H), 4.01 (s, 1H), 3.65 (s, 3H), 3.42 (m, 1H), 3.00 (m, 1H), 2.94 (m, 2H), 2.62 (m, 1H), 2.49 (m, 1H). HPLC: chiralcel OD-H 0.46 cm diam.×25 cm. n-Hexane:2-propanol (85:15), 0.5 ml/min, 254 nm. R.T. 11.4 min. HRMS (ES+) 348.1606, calculated for $C_{22}H_{21}NO_3$+H$^+$: 348.1600. [α]$^{20}_D$+51.6 (c=1, CH$_3$OH).

Example 4

(2S)-methyl 2-((3aS,6aR)-(4-oxo-5-phenyl-1,3a,4,6a-tetrahydrocyclopenta[c]pyrrol-2(1H)-yl)-2-phenylacetate

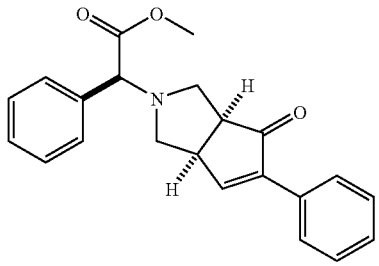

$^1$H NMR (400 MHz, CDCl3): δ (ppm) 7.72 (m, 2H), 7.63 (d, J=3 Hz, 1H), 7.42-7.28 (m, 8H), 4.05 (m, 1H), 3.66 (s, 3H), 3.38 (m, 1H), 3.16 (m, 1H), 3.00 (m, 1H), 2.69 (m, 2H), 2.51 (m, 1H). HPLC: chiralcel OD-H 0.46 cm diam.×25 cm. n-Hexane:2-propanol (85:15), 0.5 m/min, 254 nm. R.T. 17.2 min. HRMS (ES+) 348.1604, calculated for $C_{22}H_{21}NO_3$+H$^+$: 348.1600. [α]$^{20}_D$−44.4 (c=1, CH$_3$OH).

Examples 5 and 6

(2S)-methyl 2-(5-butyl oxo-1,3a,4,6a-tetrahydrocyclopenta[c]pyrrol-2(1H)-yl)-2-phenylacetate

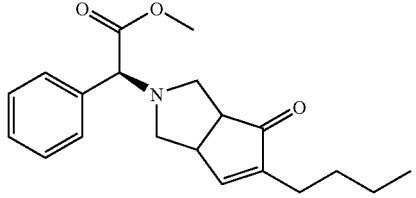

From 1-hexyne (35 mg, 0.42 mmol), CO$_2$CO$_8$ (165 mg, 0.48 mmol), (S)-methyl 2-phenyl-2-(2H-pyrrol-1(5H)-yl)acetate (70 mg, 0.32 mmol), dimethylsulphoxide (88 mg, 1.12 mmol) and 1,2-dichloroethane (2.5 ml). Flash chromatography: silica gel, hexane:ethyl acetate (2:1) afforded the product (38 mg, 36%) as yellow oil. Mixture of two diastereomers. Purification by HPLC: Chiralcel OD-H 1 cm diam.×25 cm. n-Hexane:2-propanol (97:3), 5 ml/min.

Example 5

(2S)-methyl 2-((3aR,6aS)-(5-butyl-4-oxo-1,3a,4,6a-tetrahydrocyclopenta[c]pyrrol-2(1H)-yl)-2-phenylacetate

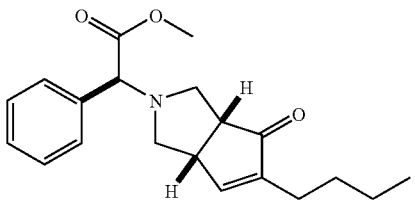

$^1$H NMR (400 MHz, CD$_3$OD): δ (ppm) 7.34 (m, 6H), 4.05 (m, 1H), 3.63 (s, 3H), 3.37 (m, 1H), 3.01 (d, J=9 Hz, 1H), 2.76 (m, 2H), 2.51 (m, 1H), 2.39 (m, 1H), 2.20 (m, 2H), 1.50 (m, 2H), 1.38 (m, 2H), 0.95 (d, J=7 Hz, 3H). HPLC: chiralcel OD-H 0.46 cm diam.×25 cm. n-Hexane:2-propanol (97:3), 0.5 ml/min, 254 nm. R.T. 9.89 min. HRMS (ES+) 328.1914, calculated for $C_{20}H_{25}NO_3$+H$^+$: 328.1913. [α]$^{20}_D$+221.4° (c=1, CHCl$_3$).

Example 6

(2S)-methyl 2-((3aS,6aR)-(5-butyl-4-oxo-1,3a,4,6a-tetrahydrocyclopenta[c]pyrrol-2(1H)-yl)-2-phenylacetate

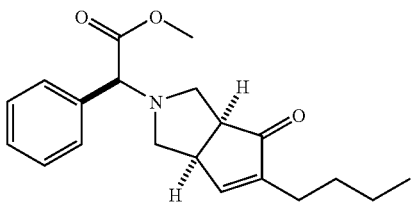

$^1$H NMR (400 MHz, CD$_3$OD): δ (ppm) 7.33 (m, 5H), 7.23 (m, 1H), 4.10 (m, 1H), 3.64 (s, 3H), 3.34 (m, 1H), 3.23 (m, 1H), 2.85 (m, 1H), 2.58 (m, 2H), 2.43 (m, 1H), 2.20 (m, 2H), 1.50 (m, 2H), 1.38 (m, 2H), 0.95 (d, J=7 Hz, 3H). HPLC: chiralcel OD-H 0.46 cm diam.×25 cm. n-Hexane:2-propanol (97:3), 0.5 ml/min, 254 nm. R.T. 13.01 min. HRMS (ES+) 328.1915, calculated for $C_{20}H_{25}NO_3$+H$^+$: 328.1913. [α]$^{20}_D$−77.5° (c=1, CHCl$_3$).

Example 27

(2S)-methyl 3-(1H-indol-3-yl)-2-((3a,6a-cis)-6-oxo-5-phenyl-3,3a,6,6a-tetrahydrocyclopenta[c]pyrrol-2(1H)-yl)propanoate

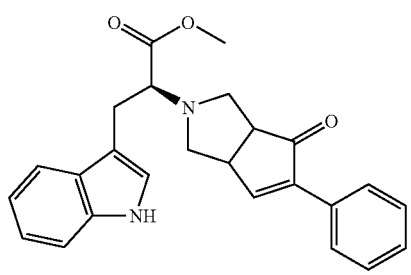

From phenylacetylene (26 mg, 0.25 mmol), $CO_2CO_8$ (92 mg, 0.27 mmol), (S)-methyl 3-(1H-indol-3-yl)-2-(2H-pyrrol-1(5H)-yl)propanoate (52 mg, 0.19 mmol), dimethylsulphoxide (60 mg, 0.77 mmol) and 1,2-dichloroethane (3 ml). Flash chromatography: silica gel, hexane:ethyl acetate (2:1) afforded the product (33 mg, 43%) as yellow oil. Mixture of two diastereomers.

$^1$H NMR (400 MHz, CDCl$_3$) diastereomeric mixture: δ (ppm) 7.83 (bs, 1H), 7.79 (bs, 1H), 7.70 (m, 4H), 7.65 (d, J=3 Hz, 2H), 7.55 (m, 2H), 7.54 (m, 1H), 7.45-7.34 (m, 6H), 7.26 (m, 2H), 7.15 (m, 2H), 7.09 (m, 2H), 6.90 (m, 2H), 3.69 (m, 1H), 3.64 (m, 1H), 3.62 (s, 3H), 3.61 (s, 3H), 3.43-3.32 (m, 3H), 3.28 (d, J=9 Hz, 1H), 3.24-3.14 (m, 2H), 3.09-2.99 (m, 3H), 2.99-2.79 (m, 7H). HRMS (ES+) 401.1852, calculated for $C_{25}H_{24}N_2O_3+H^+$: 401.1865.

Example 28

(2S)-methyl 2-((3a,6a-cis)-5-butyl-6-oxo-3,3a,6,6a-tetrahydrocyclopenta[c]pyrrol-2(1H)-yl)-3-(1H-indol-3-yl)propanoate

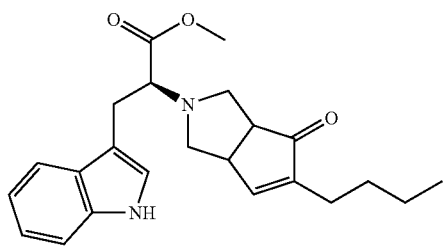

From 1-hexyne (34 mg, 0.41 mmol), $CO_2CO_8$ (280 mg, 0.82 mmol), (S)-methyl 3-(1H-indol-3-yl)-2-(2H-pyrrol-1(5H)-yl)propanoate (74 mg, 0.27 mmol), dimethylsulphoxide (106 mg, 1.36 mmol) and 1,2-dichloroethane (2.5 ml). Flash chromatography: silica gel, hexane:ethyl acetate (2:1) afforded the product (30 mg, 29%) as yellow oil. Mixture of two diastereomers.

$^1$H NMR (400 MHz, CDCl3) diastereomeric mixture: δ (ppm) 8.02 (bs, 2H), 7.54 (d, J=8 Hz, 2H), 7.31 (d, J=8 Hz, 2H), 7.19-7.06 (m, 6H), 6.93 (m, 2H), 3.61 (m, 2H), 3.57 (s, 3H), 3.55 (s, 3H), 3.29-3.13 (m, 6H), 3.07-2.99 (m, 2H), 2.90-2.67 (m, 8H), 2.16 (m, 4H), 1.44 (m, 4H), 1.34 (m, 4H), 0.92 (t, J=7 Hz, 3H), 0.91 (t, J=7 Hz, 3H). HRMS (ES+) 381.2188, calculated for $C_{23}H_{28}N_2O_3+H^+$: 381.2178.

A general overview of the examples synthesised (Formula Iaa), the starting amino acid esters (formula M) the intermediates/compounds (formula II) and the yields of the first reaction step (compound formula AA to compound formula II) and the second reaction step (compound formula II to compound formula Iaa) is given in the table below. In addition as the Pauson-Khand Reaction (second reaction step) takes place without stereocontrol leading to a 1:1 mixture of diastereomers, which can easily be separated by preparative HPLC (e.g. Chiral-cel OD-H column), the two diastereomers are given in the table as well. The two diastereomers can be differentiated as the fast- and the slow-eluting diastereomer and would show the following formulas:

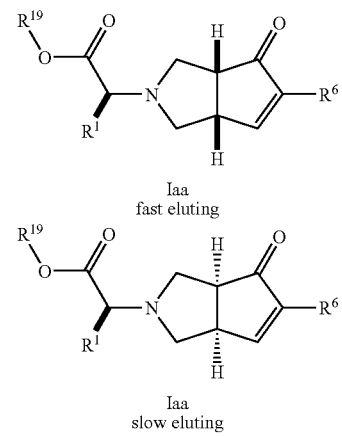

Iaa
fast eluting

Iaa
slow eluting

These structures are based on the fact that the compound according to example 20 was crystallized and submitted to X-ray diffraction, yielding its absolute configuration. This was then assigned by analogy to the other examples.

Biological Activity

Some representative compounds of the invention are tested for their activity as sigma (sigma-1 and sigma-2) inhibitors. The following protocols are followed:

Sigma-1

Brain membrane preparation and binding assays for the σ1-receptor are performed as described (DeHaven-Hudkins et al., 1992) with some modifications. In brief, guinea pig brains are homogenized in 10 vols. (w/v) of Tris-HCl 50 mM 0.32 M sucrose, pH 7.4 is centrifuged at 1000 g for 10 min at 4° C. and the supernatants collected and centrifuged again at 48000 g for 15 min at 4° C. The pellet is resuspended in 10 volumes of Tris-HCl buffer (50 mM, pH 7.4), incubated at 37° C. for 30 min, and centrifuged at 48000 g for 20 min at 4° C. Following this, the pellet is resuspended in fresh Tris-HCl buffer (50 mM, pH 7.4) and stored on ice until use.

Each assay tube contain 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding is defined by addition of a final concentration of 1 μM haloperidol. All tubes are incubated at 37° C. for 150 min before termination of the reaction by rapid filtration over Schleicher & Schuell GF 3362 glass fibre filters [previously soaked in a solution of 0.5% polyethylenimine for at least 1 h]. Filters are then washed four times with 4 mL of cold Tris-HCl buffer (50 mM, pH 7.4). Following addition of scintillation cocktail, the samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

Sigma-2

Binding studies for σ2-receptor are performed as described (Radesca et al., 1991) with some modifications. In brief, brains from sigma receptor type I (σ1) knockout mice are homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates are then centrifuged at 1000 g for 10 min at 4° C., and the supernatants are saved. The pellets are resuspended by vortexing in 2 mL/g ice-cold Tris-sucrose buffer and centrifuged again at 1000 g for 10 min. The combined 1000 g supernatants are centrifuged at 31000 g for 15 min at 4° C. The pellets are resuspended by vortexing in 3 mL/g 10 mM Tris-HCl, pH 7.4, and the suspension is kept at 25° C. for 15 min. Following centrifugation at 31000 g for 15 min, the pellets are resuspended by gentle Potter Elvehjem homogenization to a volume of 1.53 mL/g in 10 mM Tris-HCl pH 7.4.

The assay tubes contain 10 μL of [$^3$H]-DTG (final concentration of 3 nM), 400 μL of the tissue suspension (5.3 mL/g in 50 mM Tris-HCl, pH 8.0) to a final assay volume of 0.5 mL. Non-specific binding is defined by addition of a final concentration of 1 μM haloperidol. All tubes are incubated at 25° C. for 120 min before termination of the reaction by rapid filtration over Schleicher & Schuell GF 3362 glass fibre filters [previously soaked in a solution of 0.5% polyethylenimine for at least 1 h]. Filters are washed with three times with 5 mL volumes of cold Tris-HCl buffer (10 mM, pH 8.0). Following addition of scintillation cocktail samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

REFERENCES

DeHaven-Hudkins, D. L., L. C. Fleissner, and F. Y. Ford-Rice, 1992, "Characterization of the binding of [$^3$H](+)pentazocine to σ recognition sites in guinea pig brain", Eur. J. Pharmacol. 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity σ Receptor Ligands, J. Med. Chem. 34, 3065-3074.

Langa, F., Codony X., Tovar V., Lavado A., Giménez E., Cozar P., Cantero M., Dordal A., Hernández E., Pérez R., Monroy X., Zamanillo D., Guitart X., Montoliu L I., 2003, Generation and phenotypic analysis of sigma receptor type I (Sigma1) knockout mice, European Journal of Neuroscience, Vol. 18, 2188-2196.

Lowry, O. H., N. J. Rosebrough, A. L. Farr, and R. J. Randall, 1951, Protein measurement with the Folin phenol reagent, J. Biol. Chem., 193, 265.

Some of the results obtained are shown in table (I).

TABLE I

| Example | % Binding σ1 $10^{-7}$M | % Binding σ1 $10^{-8}$M |
| --- | --- | --- |
| 1 | | |
| 2 | | |
| 3 | 31.3 | 28.0 |
| 4 | 32.3 | 24.8 |
| 5 | | |
| 6 | | |
| 7 | | |
| 8 | | |
| 11 | 33.2 | 25.6 |
| 12 | 32.4 | 16.7 |
| 13 | 26.9 | 17.6 |
| 14 | 39.6 | 28.8 |

The invention claimed is:
1. A substituted bicyclic tetrahydropyrrole compound of general formula (I)

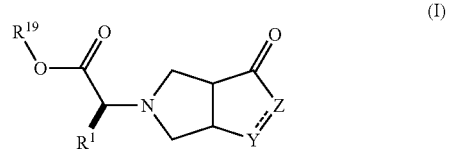

wherein
$R^1$ represents a hydrogen atom; an unbranched or branched, saturated or unsaturated, optionally at least mono-substituted aliphatic radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system or; an optionally, at least mono-substituted benzhydryl group;
wherein the bond between Y and Z may be unsaturated (Y=Z) or saturated (Y—Z);
in case of Y and Z being (Y=Z), Y represents CH and Z represents C—$R^6$; C—CHR$^7$R$^{7a}$; a C—(C=O)—$R^8$ group; a C—CH$_2$(SO$_2$)—$R^9$ group; a C—CH$_2$(SO$_2$)—NR$^{10}$R$^{10a}$ group; or a C—(C=O)—NR$^{10}$R$^{10a}$ group;
in case of Y and Z being (Y—Z), Y represents CH$_2$; C—R$^{11}$R$^{12}$; a CH—(C=O)—R$^{16}$ group; a CH—(SO$_2$)—R$^{17}$ group; CH—(SO$_2$)—NR$^{18}$R$^{18a}$ group; or a CH—(C=O)—NR$^{18}$R$^{18a}$ group and Z represents CH—R$^6$; CH—CHR$^7$R$^{7a}$; a CH—(C=O)—R$^8$ group; a CH—CH$_2$(SO$_2$)—R$^9$ group; a CH—CH$_2$(SO$_2$)—NR$^{10}$R$^{10a}$ group; or a CH—(C=O)—NR$^{10}$R$^{10a}$ group;
$R^2$, $R^3$, $R^4$, and $R^6$ represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^5$, $R^{5a}$, identical or different, represent a hydrogen atom; a linear or branched, saturated or unsaturated, optionally at least mono-substituted aliphatic group; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^7$, $R^{7a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^8$, $R^9$, $R^{13}$, $R^{14}$, $R^{15}$, $R^{16}$ and $R^{17}$ represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system or; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{10}$, $R^{10a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{11}$ and $R^{12}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system; a —{$SO_2$}—$R^{13}$-group; or a —$NR^{14}R^{15}$-group;

$R^{18}$ and $R^{18a}$, identical or different, represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system or; a branched or unbranched, saturated or unsaturated, optionally at least mono-substituted alkyl-heterocyclyl group in which the heterocyclyl group is optionally condensed with another, at least mono-substituted mono- or polycyclic ring system;

$R^{19}$ represent a hydrogen atom; a linear or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cyclyl group, which may be condensed with an optionally at least mono-substituted mono- or polycyclic ring system; a branched or unbranched alkyl-cycloalkyl group in which either the alkyl group and/or the cycloalkyl group is optionally at least mono-substituted; a branched or unbranched, saturated or unsaturated, optionally at least mono-substituted alkyl-aryl group in which the aryl group may be condensed with another, optionally at least mono-substituted mono- or polycyclic ring system; a branched or unbranched, saturated or unsaturated, optionally at least mono-substituted alkyl-heterocyclyl group in which the heterocyclyl group is optionally condensed with another, at least mono-substituted mono- or polycyclic ring system;

optionally in form of one of the stereoisomers, or a corresponding salt thereof.

2. The compound according to claim 1, according to formula Ia,

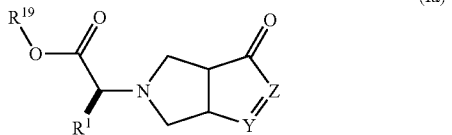

(Ia)

in which

Y represents CH and Z represents C—$R^6$; C—CHR$^7$R$^{7a}$; a C—(C=O)—R$^8$ group; a C—CH$_2$(SO$_2$)—R$^9$ group; a C—CH$_2$(SO$_2$)—NR$^{10}$R$^{10a}$ group; or a C—(C=O)—NR$^{10}$R$^{10a}$ group;

and $R^1$, $R^6$, $R^7$, $R^{7a}$, $R^8$, $R^9$, $R^{10}$, $R^{10a}$ and $R^{19}$ are defined as in claim 1.

3. The compound according to claim 1, according to formula Ib,

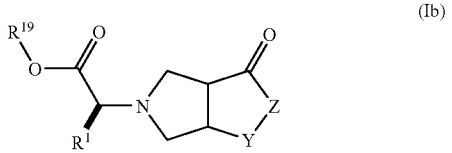

(Ib)

in which

Y represents CH$_2$; C—$R^{11}R^{12}$; a CH—(C=O)—R$^{16}$ group; a CH—(SO$_2$)—R$^{17}$ group; CH—(SO$_2$)—NR$^{18}$R$^{18a}$ group; or a CH—(C=O)—NR$^{18}$R$^{18a}$ group and Z represents CH—R$^6$; CH—CHR$^7$R$^{7a}$; a CH—(C=O)—R$^8$ group; a CH—CH$_2$(SO$_2$)—R$^9$ group; a CH—CH$_2$(SO$_2$)—NR$^{10}$R$^{10a}$ group; or a CH—(C=O)—NR$^{10}$R$^{10a}$ group;

and $R^1$, $R^6$, $R^7$, $R^{7a}$, $R^8$, $R^9$, $R^{10}$, $R^{10a}$, $R^{11}$, $R^{12}$, $R^{16}$, $R^{17}$, $R^{18}$, $R^{18a}$ and $R^{19}$, are defined as in claim 1.

4. The compound according to claim 2, characterized in that

Z represents C—$R^6$, thus leading to the compounds being of a structure according to general formula (Iaa)

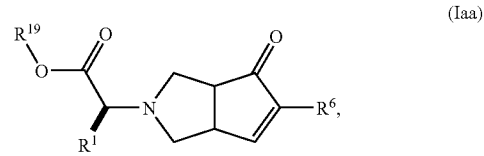

(Iaa)

with $R^1$, $R^6$ and $R^{19}$ being defined as in claim 1.

5. The compound according to claim 1, characterized in that $R^6$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system.

6. The compound according to claim 1, characterized in that $R^1$ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system.

7. The compound according to claim 1, characterized in that $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system.

8. The compound according to claim 4, according to general formula (Iaa),

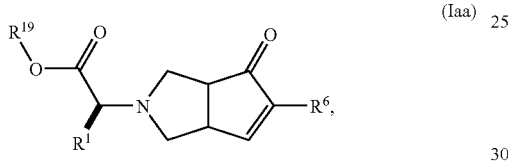

wherein

R⁶ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

and/or

R¹ represents a hydrogen atom; a linear or branched, saturated or unsaturated, optionally at least mono-substituted aliphatic group; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

and/or

R¹⁹ represents a hydrogen atom; a linear or branched, saturated or unsaturated, optionally at least mono-substituted aliphatic group; an unbranched or branched, saturated or unsaturated, optionally at least mono-substituted alkoxy radical; an optionally at least mono-substituted aryl group, which may be condensed with an optionally at least mono-substituted mono- or polycyclic ring system; a branched or unbranched, saturated or unsaturated, optionally at least mono-substituted alkyl-aryl group in which the aryl group may be condensed with another, optionally at least mono-substituted mono- or polycyclic ring system; a saturated or unsaturated, optionally at least mono-substituted, optionally at least one heteroatom as ring member containing heterocyclyl group, which may be condensed with an optionally at least mono-substituted mono- or polycyclic ring system; or a branched or unbranched, saturated or unsaturated, optionally at least mono-substituted alkyl-heterocyclyl group in which the heterocyclyl group may be condensed with another, optionally at least mono-substituted mono- or polycyclic ring system;

optionally in form of one of the stereoisomers, or a corresponding salt thereof.

9. The compound according to claim 1, selected from the group consisting of:
    (2S)-ethyl 2-(4-oxo-5-phenyl-1,3a,4,6a-tetrahydrocyclopenta[c]pyrrol-2(1H)-yl) propanoate;
    (2S)-ethyl 2-((3aR,6aS)-(4-oxo-5-phenyl-1,3a,4,6a-tetrahydrocyclopenta[c]pyrrol-2(1H)-yl) propanoate;
    (2S)-ethyl 2-((3aS,6aR)-(4-oxo-5-phenyl-1,3a,4,6a-tetrahydrocyclopenta[c]pyrrol-2(1H)-yl) propanoate;
    (2S)-ethyl 2-(5-butyl-4-oxo-1,3a,4,6a-tetrahydrocyclopenta[c]pyrrol-2(1H)-yl) propanoate;
    (2S)-ethyl 2-((3aR,6aS)-5-butyl-4-oxo-1,3a,4,6a-tetrahydrocyclopenta[c]pyrrol-2(1H)-yl) propanoate;
    (2S)-ethyl 2-((3aS,6aR)-5-butyl-4-oxo-1,3a,4,6a-tetrahydrocyclopenta[c]pyrrol-2(1H)-yl) propanoate;
    (2S)-ethyl 2-(4-oxo-5-phenyl-1,3a,4,6a-tetrahydrocyclopenta[c]pyrrol-2(1H)-yl)-3-methylbutanoate;
    (2S)-ethyl 2-((3aR,6aS)-(4-oxo-5-phenyl-1,3a,4,6a-tetrahydrocyclopenta[c]pyrrol-2(1H)-yl)-3-methylbutanoate;
    (2S)-ethyl 2-((3aS,6aR)-(4-oxo-5-phenyl-1,3a,4,6a-tetrahydrocyclopenta[c]pyrrol-2(1H)-yl)-3-methylbutanoate;
    (2S)-ethyl 2-(5-butyl-4-oxo-1,3a,4,6a-tetrahydro cyclopenta[c]pyrrol-2(1H)-yl)-3-methylbutanoate;
    (2S)-ethyl 2-((3aR,6aS)-(5-butyl-4-oxo-1,3a,4,6a-tetrahydrocyclopenta[c]pyrrol-2(1H)-yl)-3-methylbutanoate;
    (2S)-ethyl 2-((3aS,6aR)-(5-butyl-4-oxo-1,3a,4,6a-tetrahydrocyclopenta[c]pyrrol-2(1H)-yl)-3-methylbutanoate;
    (2S)-methyl 4-methyl-2-(4-oxo-5-phenyl-1,3a,4,6a-tetrahydrocyclopenta[c]pyrrol-2(1H)-yl)pentanoate;
    (2S)-methyl 4-methyl-2-((3aR,6aS)-4-oxo-5-phenyl-1,3a,4,6a-tetrahydrocyclopenta[c]pyrrol-2(1H)-yl)pentanoate;
    (2S)-methyl 4-methyl-2-((3aS,6aR)-4-oxo-5-phenyl-1,3a,4,6a-tetrahydrocyclopenta[c]pyrrol-2(1H)-yl)pentanoate;
    (2S)-methyl 2-(5-butyl-4-oxo-1,3a,4,6a-tetrahydrocyclopenta[c]pyrrol-2(1H)-yl)-4-methylpentanoate;

(2S)-methyl 2-((3aR,6aS)-(5-butyl-4-oxo-1,3a,4,6a-tetrahydro cyclopenta[c]pyrrol-2(1H)-yl)-4-methylpentanoate;

(2S)-methyl 2-((3aS,6aR)-(5-butyl-4-oxo-1,3a,4,6a-tetrahydro cyclopenta[c]pyrrol-2(1H)-yl)-4-methylpentanoate;

(2S)-methyl 2(4-oxo-5-phenyl-1,3a,4,6a-tetrahydrocyclopenta[c]pyrrol-2(1H)-yl)-3-phenylpropanoate;

(2S)-methyl 2-((3aR,6aS)-(4-oxo-5-phenyl-1,3a,4,6a-tetrahydrocyclopenta[c]pyrrol-2(1H)-yl)-3-phenylpropanoate;

(2S)-methyl 2-((3aS,6aR)-(5-butyl-4-oxo-1,3a,4,6a-tetrahydrocyclopenta[c]pyrrol-2(1H)-yl)-3-phenylpropanoate;

(2S)-methyl 2-(5-butyl-4-oxo-1,3a,4,6a-tetrahydrocyclopenta[c]pyrrol-2(1H)-yl)-3-phenylpropanoate;

(2S)-methyl 2-((3aR,6aS)-(5-butyl-4-oxo-1,3a,4,6a-tetrahydrocyclopenta[c]pyrrol-2(1H)-yl)-3-phenylpropanoate;

(2S)-methyl 2-((3aS,6aR)-(5-butyl-4-oxo-1,3a,4,6a-tetrahydrocyclopenta[c]pyrrol-2(1H)-yl)-3-phenylpropanoate;

(2S)-methyl 2-(4-oxo-5-phenyl-1,3a,4,6a-tetrahydrocyclopenta[c]pyrrol-2(1H)-yl)-2-phenylacetate;

(2S)-methyl 2-((3aR,6aS)-(4-oxo-5-phenyl-1,3a,4,6a-tetrahydrocyclopenta[c]pyrrol-2(1H)-yl)-2-phenylacetate;

(2S)-methyl 2-((3aS,6aR)-(4-oxo-5-phenyl-1,3a,4,6a-tetrahydrocyclopenta[c]pyrrol-2(1H)-yl)-2-phenylacetate;

(2S)-methyl 2-(5-butyl-4-oxo-1,3a,4,6a-tetrahydrocyclopenta[c]pyrrol-2(1H)-yl)-2-phenylacetate;

(2S)-methyl 2-((3aR,6aS)-(5-butyl-4-oxo-1,3a,4,6a-tetrahydro cyclopenta[c]pyrrol-2(1H)-yl)-2-phenylacetate;

(2S)-methyl 2-((3aS,6aR)-(5-butyl-4-oxo-1,3a,4,6a-tetrahydro cyclopenta[c]pyrrol-2(1H)-yl)-2-phenylacetate;

(2S)-methyl 3-(1H-indol-3-yl)-2-((3a,6a-cis)-6-oxo-5-phenyl-3,3a,6,6a-tetrahydrocyclopenta[c]pyrrol-2(1H)-yl)propanoate; or (2S)-methyl 2-((3a,6a-cis)-5-butyl-6-oxo-3,3a,6,6a-tetrahydrocyclopenta[c]pyrrol-2(1H)-yl)-3-(1H-indol-3-yl)propanoate;

optionally in form of one of the stereoisomers, or a corresponding salt thereof.

10. A process for the preparation of substituted bicyclic tetrahydropyrrole compounds of general formula (I) by reacting one substituted pyrroline compound of general formula (II),

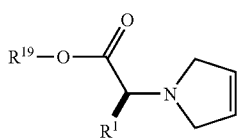

wherein
$R^1$ and $R^{19}$ have the meaning according to claim 1, is reacted with a compound of general formula (III),

wherein Z represents a $CH—R^6$ group; a $CH—CHR^7R^{7a}$ group; a $CH—(C=O)—R^8$ group; a $CH—CH_2(SO_2)—R^9$ group; a $CH—CH_2(SO_2)—NR^{10}R^{10a}$ group; or a $CH—(C=O)—NR^{10}R^{10a}$ group, to give compounds of general formula (Ia),

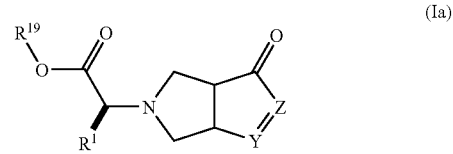

wherein the bond between Y and Z is unsaturated (Y=Z) in which Y represents a CH group and Z has the meaning according to claim 1.

11. A process for the preparation of substituted bicyclic tetrahydropyrrole compounds of general formula (I) by performing a 1,4-addition reaction with a substituted pyrroline compound of general formula (Ia),

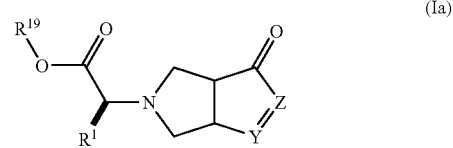

wherein $R^1$ and $R^{19}$ have the meaning according to claim 1, Z represents a $CH—R^6$ group; a $CH—CHR^7R^{7a}$ group; a $CH—(C=O)—R^8$ group; a $CH—CH_2(SO_2)—R^9$ group; a $CH—CH_2(SO_2)—NR^{10}R^{10a}$ group; or a $CH—(C=O)—NR^{10}R^{10a}$ group and Y represents a CH group, to give a compound of general formula (Ib),

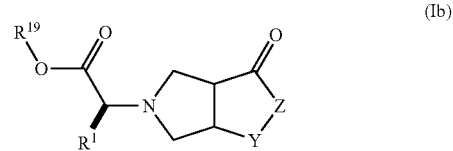

wherein $R^1$ and $R^{19}$ have the meaning according to claim 1, Y and Z form a saturated (Y—Z) bond, and Y represents a $CH_2$ group; a $C—R^{11}R^{12}$ group; a $CH—(C=O)—R^{16}$ group; a $CH—(SO_2)—R^{17}$ group; $CH—(SO_2)—NR^{18}R^{18a}$ group; or a $CH—(C=O)—NR^{18}R^{18a}$ group.

12. A medicament comprising at least one substituted bicyclic tetrahydropyrrole compound of general formula (I), according to claim 1, said compound being optionally a stereoisomer, preferably an enantiomer; or a corresponding salt thereof; or a prodrug form thereof.

13. A method for the manufacture of a medicament which comprises admixing with a carrier at least one compound of general formula (I) according to claim 1, said compound being optionally a stereoisomer; or a corresponding salt thereof; or a prodrug form thereof.

14. A compound according to claim 1, wherein the compound is the form of an enantiomer, diastereomer, racemate, or in form of a mixture of at least two of the stereoisomers in any ratio.

15. A compound according to claim 5, wherein $R^6$ represents a hydrogen atom; a linear or branched, saturated or unsaturated, optionally at least mono-substituted aliphatic group; or an optionally at least mono-substituted aryl group, which may be condensed with an optionally at least mono-substituted mono- or polycyclic ring system.

16. A compound according to claim 5, wherein $R^6$ represents a hydrogen atom; a linear or branched, saturated, optionally at least mono-substituted aliphatic group; or an optionally at least mono-substituted aryl group.

17. A compound according to claim 5, wherein $R^6$ represents a linear or branched, saturated or unsaturated, optionally at least mono-substituted $C_{1-6}$-alkyl group; or an optionally at least mono-substituted phenyl group.

18. A compound according to claim 6, wherein $R^1$ represents a hydrogen atom; a linear or branched, saturated or unsaturated, optionally at least mono-substituted aliphatic group; an optionally at least mono-substituted aryl group, which may be condensed with an optionally substituted mono-substituted mono- or polycyclic ring system; an branched or unbranched, saturated or unsaturated, optionally at least mono-substituted alkyl-aryl group in which the aryl group may be condensed with another, optionally at least mono-substituted mono- or polycyclic ring system; or a branched or unbranched, saturated or unsaturated, optionally at least mono-substituted alkyl-heterocyclyl group in which the heterocyclyl group may be condensed with another, an optionally at least mono-substituted mono- or polycyclic ring system.

19. A compound according to claim 6, wherein $R^1$ represents a hydrogen atom; a linear or branched, saturated, optionally at least mono-substituted aliphatic group; an optionally at least mono-substituted aryl group; an optionally at least mono-substituted alkyl-aryl group; or an optionally at least mono-substituted alkyl-heterocyclyl group.

20. A compound according to claim 6, wherein $R^1$ represents a linear or branched, saturated, optionally at least mono-substituted $C_{1-6}$-alkyl group; an optionally at least mono-substituted phenyl group; an optionally at least mono-substituted benzyl group; or an optionally at least mono-substituted $CH_2$-heterocyclyl group.

21. A compound according to claim 7, wherein $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; or an optionally at least mono-substituted aryl group, which may be condensed with an optionally at least mono-substituted mono- or polycyclic ring system.

22. A compound according to claim 7, wherein $R^{19}$ represents a hydrogen atom; a linear or branched, saturated, optionally at least mono-substituted aliphatic group; an unbranched or branched, saturated or unsaturated, optionally at least mono-substituted alkoxy radical; or an optionally at least mono-substituted aryl group.

23. A compound according to claim 7, wherein $R^{19}$ represents a linear or branched, saturated, optionally at least mono-substituted $C_{1-4}$-alkyl group; or an optionally at least mono-substituted phenyl group.

24. A compound according to claim 8, wherein $R^6$ represents a hydrogen atom; a linear or branched, saturated or unsaturated, optionally at least mono-substituted aliphatic group; or an optionally at least mono-substituted aryl group, which may be condensed with an optionally at least mono-substituted mono- or polycyclic ring system.

25. A compound according to claim 8, wherein $R^6$ represents a hydrogen atom; a linear or branched, saturated, optionally at least mono-substituted aliphatic group; or an optionally at least mono-substituted aryl group.

26. A compound according to claim 8, wherein $R^6$ represents a linear or branched, saturated, optionally at least mono-substituted $C_{1-6}$-alkyl group; or an optionally at least mono-substituted phenyl group.

27. A compound according to claim 8, wherein $R^1$ represents a hydrogen atom; a linear or branched, saturated or unsaturated, optionally at least mono-substituted aliphatic group; an optionally at least mono-substituted aryl group, which may be condensed with an optionally substituted mono-substituted mono- or polycyclic ring system; an branched or unbranched, saturated or unsaturated, optionally at least mono-substituted alkyl-aryl group in which the aryl group may be condensed with another, optionally at least mono-substituted mono- or polycyclic ring system; or a branched or unbranched, saturated or unsaturated, optionally at least mono-substituted alkyl-heterocyclyl group in which the heterocyclyl group may be condensed with another, an optionally at least mono-substituted mono- or polycyclic ring system.

28. A compound according to claim 8, wherein $R^1$ represents a hydrogen atom; a linear or branched, saturated, optionally at least mono-substituted aliphatic group; an optionally at least mono-substituted aryl group; an optionally at least mono-substituted alkyl-aryl group; or an optionally at least mono-substituted alkyl-heterocyclyl group.

29. A compound according to claim 8, wherein $R^1$ represents a linear or branched, saturated, optionally at least mono-substituted $C_{1-6}$-alkyl group; an optionally at least mono-substituted phenyl group; an optionally at least mono-substituted benzyl group; or an optionally at least mono-substituted $CH_2$-heterocyclyl group.

30. A compound according to claim 8, wherein $R^{19}$ represents a hydrogen atom; a linear or branched, saturated or unsaturated, optionally at least mono-substituted aliphatic group; an unbranched or branched, saturated or unsaturated, optionally at least mono-substituted alkoxy radical; or an optionally at least mono-substituted aryl group, which may be condensed with an optionally at least mono-substituted mono- or polycyclic ring system.

31. A compound according to claim 8, wherein $R^{19}$ represents a hydrogen atom; a linear or branched, saturated, optionally at least mono-substituted aliphatic group; an unbranched or branched, saturated or unsaturated, optionally at least mono-substituted alkoxy radical; or an optionally at least mono-substituted aryl group.

32. A compound according to claim 8, wherein $R^{19}$ represents a linear or branched, saturated, optionally at least mono-substituted $C_{1-4}$-alkyl group; or an optionally at least mono-substituted phenyl group.

33. A compound according to claim 8, wherein the stereoisomers are in the form of enantiomers, diastereomers, a racemate, or in form of a mixture of at least two of the enantiomers and/or diastereomers, in any mixing ratio.

34. A compound according to claim 9, wherein the stereoisomers are in the form of enantiomers, diastereomers, a racemate, or in form of a mixture of at least two of the enantiomers and/or diastereomers, in any mixing ratio.

35. A medicament according to claim 12, wherein the stereoisomers are in the form of enantiomers, diastereomers, a racemate, or in form of a mixture of at least two of the enantiomers and/or diastereomers, in any mixing ratio.

36. A method according to claim 13, wherein the stereoisomers are in the form of enantiomers, diastereomers, a racemate, or in form of a mixture of at least two of the enantiomers and/or diastereomers, in any mixing ratio.

* * * * *